(12) United States Patent
Hendrick et al.

(10) Patent No.: US 10,383,691 B2
(45) Date of Patent: Aug. 20, 2019

(54) LAST CATHETER WITH HELICAL INTERNAL LUMEN

(71) Applicant: The Spectranetics Corporation, Colorado Springs, CO (US)

(72) Inventors: Brandon Thomas Hendrick, Colorado Springs, CO (US); Kenneth P. Grace, Woodland Park, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 836 days.

(21) Appl. No.: 13/800,675

(22) Filed: Mar. 13, 2013

(65) Prior Publication Data

US 2014/0276682 A1    Sep. 18, 2014

(51) Int. Cl.
*A61B 18/24*    (2006.01)
*A61M 1/00*    (2006.01)

(52) U.S. Cl.
CPC .......... *A61B 18/245* (2013.01); *A61M 1/008* (2013.01)

(58) Field of Classification Search
CPC . A61B 17/22; A61B 17/3203; A61B 17/3207; A61B 18/20; A61B 18/22; A61B 18/24; A61B 1/00163; A61B 1/12
USPC ........... 606/2, 7, 159, 180, 200; 607/80, 88, 607/122, 127; 600/300
See application file for complete search history.

(56) References Cited

U.S. PATENT DOCUMENTS

| | | |
|---|---|---|
| 1,663,761 A | 3/1928 | Johnson |
| 3,400,708 A | 9/1968 | Scheidt |
| 3,472,234 A | 10/1969 | Tachick |
| 3,498,286 A | 3/1970 | Innis et al. |
| 3,614,953 A | 10/1971 | Moss |
| 4,051,596 A | 10/1977 | Hofmann |
| 4,203,444 A | 5/1980 | Bonnell et al. |
| 4,227,770 A | 10/1980 | Gunn |
| 4,246,902 A | 1/1981 | Martinez |
| 4,274,414 A | 6/1981 | Johnson et al. |
| 4,388,800 A | 6/1983 | Trezeguet et al. |
| 4,471,777 A | 9/1984 | McCorkle |
| 4,517,977 A | 5/1985 | Frost |
| 4,573,965 A * | 3/1986 | Russo ............................ 604/30 |
| 4,576,146 A | 3/1986 | Kawazoe et al. |

(Continued)

FOREIGN PATENT DOCUMENTS

| JP | H05-506382 | 9/1993 |
|---|---|---|
| JP | 2004-516073 | 6/2004 |

(Continued)

OTHER PUBLICATIONS

U.S. Appl. No. 13/800,651, filed Mar. 13, 2013, Hendrick et al.

(Continued)

*Primary Examiner* — William J Levicky
*Assistant Examiner* — Qingjun Kong

(57) ABSTRACT

Catheters for ablation and removal of occlusions from blood vessels are provided. Laser cutting systems and mechanical cutting systems are provided in catheter devices, the cutting systems operable to ablate, cut, dislodge, and otherwise remove occlusions within a blood vessel that may limit or prevent proper circulation. A helical or partially-helical inner surface structure is provided in the catheter, the structure operable to remove or translate dislodged material(s).

8 Claims, 8 Drawing Sheets

(56) References Cited

U.S. PATENT DOCUMENTS

| | | |
|---|---|---|
| 4,582,056 A | 4/1986 | McCorkle |
| 4,587,972 A | 5/1986 | Morantte et al. |
| 4,598,710 A | 7/1986 | Kleinberg et al. |
| 4,646,738 A | 3/1987 | Trott |
| 4,662,869 A | 5/1987 | Wright |
| 4,674,502 A | 6/1987 | Imonti |
| 4,729,763 A | 3/1988 | Henrie |
| 4,754,755 A | 7/1988 | Husted |
| 4,767,403 A | 8/1988 | Hodge |
| 4,784,132 A * | 11/1988 | Fox .................. A61B 18/20 606/15 |
| 4,848,339 A * | 7/1989 | Rink .................. A61B 18/28 606/15 |
| 4,943,289 A | 7/1990 | Goode et al. |
| 4,950,232 A | 8/1990 | Ruzicka et al. |
| 4,950,277 A | 8/1990 | Farr |
| 4,955,882 A | 9/1990 | Hakky |
| 4,988,347 A | 1/1991 | Goode et al. |
| 5,011,482 A | 4/1991 | Goode et al. |
| 5,013,310 A | 5/1991 | Goode et al. |
| 5,031,634 A | 7/1991 | Simon |
| 5,041,084 A | 8/1991 | DeVries et al. |
| 5,061,266 A | 10/1991 | Hakky |
| 5,100,425 A | 3/1992 | Fischell et al. |
| 5,116,317 A | 5/1992 | Carson et al. |
| 5,152,744 A | 10/1992 | Krause et al. |
| 5,201,316 A | 4/1993 | Pomeranz et al. |
| 5,207,683 A | 5/1993 | Goode et al. |
| 5,243,679 A | 9/1993 | Sharrow et al. |
| 5,250,045 A | 10/1993 | Bohley |
| 5,261,877 A | 11/1993 | Fine et al. |
| 5,263,928 A | 11/1993 | Trauthen et al. |
| 5,275,609 A | 1/1994 | Pingleton et al. |
| 5,290,275 A | 3/1994 | Kittrell et al. |
| 5,290,280 A | 3/1994 | Daikuzono |
| 5,290,303 A | 3/1994 | Pingleton et al. |
| 5,328,488 A | 7/1994 | Daikuzono |
| 5,383,199 A | 1/1995 | Laudenslager et al. |
| 5,395,328 A | 3/1995 | Ockuly et al. |
| 5,415,653 A | 5/1995 | Wardle et al. |
| 5,423,330 A | 6/1995 | Lee |
| 5,423,740 A | 6/1995 | Sullivan et al. |
| 5,423,806 A * | 6/1995 | Dale .................. A61B 18/24 606/15 |
| 5,451,221 A | 9/1995 | Cho et al. |
| 5,456,680 A | 10/1995 | Taylor et al. |
| 5,463,712 A | 10/1995 | Cawood |
| 5,484,433 A | 1/1996 | Taylor et al. |
| 5,507,751 A | 4/1996 | Goode et al. |
| 5,531,741 A | 7/1996 | Barbacci |
| 5,536,242 A * | 7/1996 | Willard ............ A61B 17/32037 604/22 |
| 5,562,694 A | 10/1996 | Sauer et al. |
| 5,569,284 A | 10/1996 | Young et al. |
| 5,575,797 A | 11/1996 | Neubauer et al. |
| 5,620,451 A | 4/1997 | Rosborough |
| 5,632,749 A | 5/1997 | Goode et al. |
| 5,651,781 A | 7/1997 | Grace |
| 5,651,783 A | 7/1997 | Reynard |
| 5,697,936 A | 12/1997 | Shipko et al. |
| 5,713,860 A | 2/1998 | Kaplan et al. |
| 5,718,237 A | 2/1998 | Haaga |
| 5,725,523 A | 3/1998 | Mueller |
| 5,766,164 A | 6/1998 | Mueller et al. |
| 5,782,823 A | 7/1998 | Mueller |
| 5,807,399 A | 9/1998 | Laske et al. |
| 5,814,044 A | 9/1998 | Hooven |
| 5,823,971 A | 10/1998 | Robinson et al. |
| 5,824,026 A | 10/1998 | Diaz |
| 5,830,209 A | 11/1998 | Savage et al. |
| 5,863,294 A | 1/1999 | Alden |
| 5,873,865 A | 2/1999 | Horzewski et al. |
| 5,873,886 A | 2/1999 | Larsen et al. |
| 5,879,365 A | 3/1999 | Whitfield et al. |
| 5,893,862 A | 4/1999 | Pratt et al. |
| 5,899,915 A | 5/1999 | Saadat |
| 5,910,150 A | 6/1999 | Saadat |
| 5,916,210 A | 6/1999 | Winston |
| 5,931,848 A | 8/1999 | Saadat |
| 5,941,893 A | 8/1999 | Saadat |
| 5,951,581 A | 9/1999 | Saadat et al. |
| 5,972,012 A | 10/1999 | Ream et al. |
| 5,980,515 A | 11/1999 | Tu |
| 5,980,545 A | 11/1999 | Pacala et al. |
| 6,007,512 A | 12/1999 | Hooven |
| 6,010,476 A | 1/2000 | Saadat |
| 6,019,756 A | 2/2000 | Mueller et al. |
| 6,022,336 A | 2/2000 | Zadno-Azizi et al. |
| 6,024,751 A | 2/2000 | Lovato et al. |
| 6,027,497 A | 2/2000 | Daniel et al. |
| 6,033,402 A | 3/2000 | Tu et al. |
| 6,036,685 A | 3/2000 | Mueller |
| 6,051,008 A | 4/2000 | Saadat et al. |
| 6,053,900 A | 4/2000 | Brown et al. |
| 6,066,131 A | 5/2000 | Mueller et al. |
| 6,080,175 A | 6/2000 | Hogendijk |
| 6,083,237 A | 7/2000 | Huitema et al. |
| 6,096,028 A | 8/2000 | Bahmanyar et al. |
| 6,099,537 A | 8/2000 | Sugai et al. |
| 6,102,926 A | 8/2000 | Tartaglia et al. |
| 6,117,149 A | 9/2000 | Sorensen et al. |
| 6,120,520 A | 9/2000 | Saadat et al. |
| 6,126,654 A | 10/2000 | Giba et al. |
| 6,136,005 A | 10/2000 | Goode et al. |
| 6,139,543 A | 10/2000 | Esch et al. |
| 6,152,909 A | 11/2000 | Bagaoisan et al. |
| 6,152,918 A | 11/2000 | Padilla et al. |
| 6,156,049 A | 12/2000 | Lovato et al. |
| 6,159,203 A | 12/2000 | Sinofsky |
| 6,159,225 A | 12/2000 | Makower |
| 6,162,214 A | 12/2000 | Mueller et al. |
| 6,165,188 A | 12/2000 | Saadat et al. |
| 6,167,315 A | 12/2000 | Coe et al. |
| 6,174,307 B1 | 1/2001 | Daniel et al. |
| 6,190,352 B1 | 2/2001 | Haarala et al. |
| 6,190,353 B1 | 2/2001 | Makower et al. |
| 6,203,537 B1 | 3/2001 | Adrian |
| 6,210,400 B1 | 4/2001 | Hebert et al. |
| 6,210,402 B1 | 4/2001 | Olsen et al. |
| 6,228,076 B1 | 5/2001 | Winston et al. |
| 6,233,474 B1 | 5/2001 | Lemelson |
| 6,235,044 B1 | 5/2001 | Root et al. |
| 6,241,692 B1 | 6/2001 | Tu et al. |
| 6,245,011 B1 | 6/2001 | Dudda et al. |
| 6,251,121 B1 | 6/2001 | Saadat |
| 6,258,083 B1 | 7/2001 | Daniel et al. |
| 6,290,668 B1 | 9/2001 | Gregory et al. |
| 6,315,774 B1 | 11/2001 | Daniel et al. |
| 6,324,434 B2 | 11/2001 | Coe et al. |
| 6,368,318 B1 | 4/2002 | Visuri et al. |
| 6,395,002 B1 | 5/2002 | Ellman et al. |
| 6,398,773 B1 | 6/2002 | Bagaoisan et al. |
| 6,402,771 B1 | 6/2002 | Palmer et al. |
| 6,402,781 B1 | 6/2002 | Langberg et al. |
| 6,419,674 B1 | 7/2002 | Bowser et al. |
| 6,419,684 B1 | 7/2002 | Heisler et al. |
| 6,423,051 B1 | 7/2002 | Kaplan et al. |
| 6,428,539 B1 | 8/2002 | Baxter et al. |
| 6,428,556 B1 | 8/2002 | Chin |
| 6,432,119 B1 | 8/2002 | Saadat |
| 6,436,054 B1 | 8/2002 | Viola et al. |
| 6,436,114 B1 | 8/2002 | Novak et al. |
| 6,440,124 B1 | 8/2002 | Esch et al. |
| 6,440,125 B1 * | 8/2002 | Rentrop .............. A61B 18/245 128/898 |
| 6,447,525 B2 | 9/2002 | Follmer et al. |
| 6,454,741 B1 | 9/2002 | Muni et al. |
| 6,454,758 B1 | 9/2002 | Thompson et al. |
| 6,461,349 B1 | 10/2002 | Elbrecht et al. |
| 6,478,777 B1 | 11/2002 | Honeck et al. |
| 6,488,636 B2 | 12/2002 | Bryan et al. |
| 6,500,182 B2 | 12/2002 | Foster |
| 6,512,959 B1 | 1/2003 | Gomperz et al. |
| 6,527,752 B1 | 3/2003 | Bosley, Jr. |

(56) References Cited

U.S. PATENT DOCUMENTS

| | | |
|---|---|---|
| 6,537,314 B2 | 3/2003 | Langberg et al. |
| 6,540,865 B1 | 4/2003 | Miekka et al. |
| 6,547,779 B2 | 4/2003 | Levine et al. |
| 6,554,779 B2 | 4/2003 | Viola et al. |
| 6,558,382 B2 | 5/2003 | Jahns et al. |
| 6,565,588 B1 | 5/2003 | Clement et al. |
| 6,569,082 B1 | 5/2003 | Chin |
| 6,575,997 B1 | 6/2003 | Palmer et al. |
| 6,592,607 B1 | 7/2003 | Palmer et al. |
| 6,595,982 B2 | 7/2003 | Sekino et al. |
| 6,599,296 B1 | 7/2003 | Gillick et al. |
| 6,602,241 B2 | 8/2003 | Makower et al. |
| 6,607,547 B1 | 8/2003 | Chin |
| 6,610,046 B1 | 8/2003 | Usami et al. |
| 6,610,066 B2 | 8/2003 | Dinger et al. |
| 6,613,013 B2 | 9/2003 | Haarala et al. |
| 6,620,153 B2 | 9/2003 | Mueller et al. |
| 6,620,160 B2 | 9/2003 | Lewis et al. |
| 6,620,180 B1 | 9/2003 | Bays et al. |
| 6,641,590 B1 | 11/2003 | Palmer et al. |
| 6,652,480 B1 | 11/2003 | Imran et al. |
| 6,652,548 B2 | 11/2003 | Evans et al. |
| 6,660,021 B1 | 12/2003 | Palmer et al. |
| 6,663,626 B2 | 12/2003 | Truckai et al. |
| 6,669,685 B1 | 12/2003 | Rizoiu et al. |
| 6,673,090 B2 | 1/2004 | Root et al. |
| 6,687,548 B2 | 2/2004 | Goode |
| 6,702,813 B1 | 3/2004 | Baxter et al. |
| 6,706,018 B2 | 3/2004 | Westlund et al. |
| 6,706,052 B1 | 3/2004 | Chin |
| 6,706,065 B2 | 3/2004 | Langberg et al. |
| 6,709,456 B2 | 3/2004 | Langberg et al. |
| 6,712,773 B1 | 3/2004 | Viola |
| 6,712,826 B2 | 3/2004 | Lui |
| 6,772,014 B2 | 8/2004 | Coe et al. |
| 6,802,838 B2 | 10/2004 | Loeb et al. |
| 6,805,692 B2 | 10/2004 | Muni et al. |
| 6,810,882 B2 | 11/2004 | Langberg et al. |
| 6,818,001 B2 | 11/2004 | Wulfman et al. |
| 6,860,860 B2 | 3/2005 | Viola |
| 6,871,085 B2 | 3/2005 | Sommer |
| 6,879,761 B2 | 4/2005 | Rogers |
| 6,884,240 B1 | 4/2005 | Dykes |
| 6,887,238 B2 | 5/2005 | Jahns et al. |
| 6,893,450 B2 | 5/2005 | Foster |
| 6,913,612 B2 | 7/2005 | Palmer et al. |
| 6,962,585 B2 | 11/2005 | Poleo, Jr. |
| 6,979,290 B2 | 12/2005 | Mourlas et al. |
| 6,979,319 B2 | 12/2005 | Manning et al. |
| 6,989,028 B2 | 1/2006 | Lashinski et al. |
| 6,999,809 B2 | 2/2006 | Currier et al. |
| 7,004,956 B2 | 2/2006 | Palmer et al. |
| 7,011,682 B2 | 3/2006 | Lashinski et al. |
| 7,022,133 B2 | 4/2006 | Yee et al. |
| 7,033,335 B2 | 4/2006 | Haarala et al. |
| 7,033,344 B2 | 4/2006 | Imran |
| 7,033,357 B2 | 4/2006 | Baxter et al. |
| 7,060,061 B2 | 6/2006 | Altshuler et al. |
| 7,063,693 B2 | 6/2006 | Guenst |
| 7,077,856 B2 | 7/2006 | Whitman |
| 7,092,765 B2 | 8/2006 | Geske et al. |
| 7,097,120 B2 | 8/2006 | Marino |
| 7,097,129 B2 | 8/2006 | Matthies |
| 7,104,983 B2 | 9/2006 | Grasso, III et al. |
| 7,114,642 B2 | 10/2006 | Whitman |
| 7,117,039 B2 | 10/2006 | Manning et al. |
| 7,149,587 B2 | 12/2006 | Wardle et al. |
| 7,151,965 B2 | 12/2006 | Osypka |
| 7,189,207 B2 | 3/2007 | Viola |
| 7,191,015 B2 | 3/2007 | Lamson et al. |
| 7,192,430 B2 | 3/2007 | Truckai et al. |
| 7,204,824 B2 | 4/2007 | Moulis |
| 7,214,180 B2 | 5/2007 | Chin |
| 7,226,459 B2 | 6/2007 | Cesarini et al. |
| 7,238,179 B2 | 7/2007 | Brucker et al. |
| 7,238,180 B2 | 7/2007 | Mester et al. |
| 7,252,641 B2 | 8/2007 | Thompson et al. |
| 7,264,587 B2 | 9/2007 | Chin |
| 7,273,478 B2 | 9/2007 | Appling et al. |
| 7,276,052 B2 | 10/2007 | Kobayashi et al. |
| 7,288,096 B2 | 10/2007 | Chin |
| 7,296,577 B2 | 11/2007 | Lashinski et al. |
| 7,306,588 B2 | 12/2007 | Loeb et al. |
| 7,326,226 B2 | 2/2008 | Root et al. |
| 7,328,071 B1 | 2/2008 | Stehr et al. |
| 7,344,546 B2 | 3/2008 | Wulfman et al. |
| 7,357,794 B2 | 4/2008 | Makower et al. |
| 7,359,756 B2 | 4/2008 | Goode |
| 7,369,901 B1 | 5/2008 | Morgan et al. |
| 7,392,095 B2 | 6/2008 | Flynn et al. |
| 7,396,354 B2 | 7/2008 | Rychnovsky et al. |
| 7,398,781 B1 | 7/2008 | Chin |
| 7,435,247 B2 | 10/2008 | Woloszko et al. |
| 7,449,010 B1 | 11/2008 | Hayase et al. |
| 7,462,167 B2 | 12/2008 | Kratz et al. |
| 7,485,127 B2 | 2/2009 | Nistal |
| 7,494,484 B2 | 2/2009 | Beck et al. |
| 7,507,252 B2 | 3/2009 | Lashinski et al. |
| 7,509,169 B2 | 3/2009 | Eigler et al. |
| 7,510,576 B2 | 3/2009 | Langberg et al. |
| 7,513,877 B2 | 4/2009 | Viola |
| 7,513,892 B1 | 4/2009 | Haarala et al. |
| 7,526,342 B2 | 4/2009 | Chin et al. |
| 7,537,602 B2 | 5/2009 | Whitman |
| 7,540,865 B2 | 6/2009 | Griffin |
| 7,544,197 B2 | 6/2009 | Kelsch et al. |
| 7,559,941 B2 | 7/2009 | Zannis et al. |
| D600,792 S | 9/2009 | Eubanks et al. |
| 7,591,790 B2 | 9/2009 | Pflueger |
| 7,597,698 B2 | 10/2009 | Chin |
| 7,606,615 B2 | 10/2009 | Makower et al. |
| 7,611,474 B2 | 11/2009 | Hibner et al. |
| 7,625,337 B2 | 12/2009 | Campbell et al. |
| 7,637,904 B2 | 12/2009 | Wingler et al. |
| 7,645,286 B2 | 1/2010 | Catanese et al. |
| 7,648,466 B2 | 1/2010 | Stephens et al. |
| 7,651,503 B1 | 1/2010 | Coe et al. |
| 7,651,504 B2 | 1/2010 | Goode et al. |
| D610,259 S | 2/2010 | Way et al. |
| D611,146 S | 3/2010 | Way et al. |
| 7,674,272 B2 | 3/2010 | Torrance et al. |
| 7,695,485 B2 | 4/2010 | Whitman et al. |
| 7,695,512 B2 | 4/2010 | Lashinski et al. |
| 7,697,996 B2 | 4/2010 | Manning et al. |
| 7,713,231 B2 | 5/2010 | Wulfman et al. |
| 7,713,235 B2 | 5/2010 | Torrance et al. |
| 7,713,281 B2 | 5/2010 | Leeflang et al. |
| 7,722,549 B2 | 5/2010 | Nakao |
| 7,740,626 B2 | 6/2010 | Takayama et al. |
| 7,743,960 B2 | 6/2010 | Whitman et al. |
| D619,252 S | 7/2010 | Way et al. |
| D619,253 S | 7/2010 | Way et al. |
| 7,758,594 B2 | 7/2010 | Lamson et al. |
| 7,758,613 B2 | 7/2010 | Whitman |
| D621,939 S | 8/2010 | Way et al. |
| 7,766,923 B2 | 8/2010 | Catanese et al. |
| 7,780,682 B2 | 8/2010 | Catanese et al. |
| 7,780,694 B2 | 8/2010 | Palmer et al. |
| 7,794,411 B2 | 9/2010 | Ritchart et al. |
| 7,798,813 B1 | 9/2010 | Harrel |
| 7,803,151 B2 | 9/2010 | Whitman |
| 7,806,835 B2 | 10/2010 | Hibner et al. |
| 7,811,281 B1 | 10/2010 | Rentrop |
| 7,815,655 B2 | 10/2010 | Catanese et al. |
| 7,842,009 B2 | 11/2010 | Torrance et al. |
| 7,845,538 B2 | 12/2010 | Whitman |
| 7,858,038 B2 | 12/2010 | Andreyko et al. |
| 7,875,018 B2 | 1/2011 | Tockman et al. |
| 7,875,049 B2 | 1/2011 | Eversull et al. |
| 7,890,186 B2 | 2/2011 | Wardle et al. |
| 7,890,192 B1 | 2/2011 | Kelsch et al. |
| 7,896,879 B2 | 3/2011 | Solsberg et al. |
| 7,896,891 B2 | 3/2011 | Catanese et al. |
| 7,905,889 B2 | 3/2011 | Catanese et al. |

(56) References Cited

U.S. PATENT DOCUMENTS

| | | |
|---|---|---|
| 7,909,836 B2 | 3/2011 | McLean et al. |
| 7,914,464 B2 | 3/2011 | Burdorff et al. |
| 7,914,542 B2 | 3/2011 | Lamson et al. |
| D635,671 S | 4/2011 | Way et al. |
| 7,918,230 B2 | 4/2011 | Whitman et al. |
| 7,918,803 B2 | 4/2011 | Ritchart et al. |
| 7,922,654 B2 | 4/2011 | Boutillette et al. |
| 7,930,040 B1 | 4/2011 | Kelsch et al. |
| 7,935,146 B2 | 5/2011 | Langberg et al. |
| 7,938,786 B2 | 5/2011 | Ritchie et al. |
| 7,942,830 B2 | 5/2011 | Solsberg et al. |
| 7,951,071 B2 | 5/2011 | Whitman et al. |
| 7,951,158 B2 | 5/2011 | Catanese et al. |
| 7,959,608 B2 | 6/2011 | Nash et al. |
| 7,963,040 B2 | 6/2011 | Shan et al. |
| 7,963,433 B2 | 6/2011 | Whitman et al. |
| 7,971,800 B2 | 7/2011 | Combs et al. |
| 7,974,710 B2 | 7/2011 | Seifert |
| 7,981,049 B2 | 7/2011 | Ritchie et al. |
| 7,981,050 B2 | 7/2011 | Ritchart et al. |
| 7,981,128 B2 | 7/2011 | To et al. |
| 7,988,726 B2 | 8/2011 | Langberg et al. |
| 7,991,258 B2 | 8/2011 | Temelkuran et al. |
| 7,992,758 B2 | 8/2011 | Whitman et al. |
| 7,993,350 B2 | 8/2011 | Ventura et al. |
| 7,993,351 B2 | 8/2011 | Worley et al. |
| 7,993,359 B1 | 8/2011 | Atwell et al. |
| 8,007,469 B2 | 8/2011 | Duffy |
| 8,007,488 B2 | 8/2011 | Ravenscroft |
| 8,007,503 B2 | 8/2011 | Catanese et al. |
| 8,007,506 B2 | 8/2011 | To et al. |
| 8,016,748 B2 | 9/2011 | Mourlas et al. |
| 8,016,844 B2 | 9/2011 | Privitera et al. |
| 8,016,855 B2 | 9/2011 | Whitman et al. |
| 8,016,858 B2 | 9/2011 | Whitman |
| 8,021,373 B2 | 9/2011 | Whitman et al. |
| 8,025,199 B2 | 9/2011 | Whitman et al. |
| 8,043,309 B2 | 10/2011 | Catanese et al. |
| RE42,959 E | 11/2011 | Saadat et al. |
| 8,052,616 B2 | 11/2011 | Andrisek et al. |
| 8,052,659 B2 | 11/2011 | Ravenscroft et al. |
| 8,056,786 B2 | 11/2011 | Whitman et al. |
| 8,056,791 B2 | 11/2011 | Whitman |
| 8,070,762 B2 | 12/2011 | Escudero et al. |
| 8,090,430 B2 | 1/2012 | Makower et al. |
| 8,097,012 B2 | 1/2012 | Kagarise |
| 8,100,920 B2 | 1/2012 | Gambale et al. |
| 8,118,208 B2 | 2/2012 | Whitman |
| 8,126,570 B2 | 2/2012 | Manning et al. |
| 8,128,577 B2 | 3/2012 | Viola |
| 8,128,636 B2 | 3/2012 | Lui et al. |
| 8,133,214 B2 | 3/2012 | Hayase et al. |
| 8,137,377 B2 | 3/2012 | Palmer et al. |
| 8,142,442 B2 | 3/2012 | Palmer et al. |
| 8,142,446 B2 | 3/2012 | Shan |
| RE43,300 E | 4/2012 | Saadat et al. |
| 8,157,815 B2 | 4/2012 | Catanese et al. |
| 8,162,878 B2 | 4/2012 | Bonnette et al. |
| 8,186,559 B1 | 5/2012 | Whitman |
| 8,187,204 B2 | 5/2012 | Miller et al. |
| 8,192,430 B2 | 6/2012 | Goode et al. |
| 8,202,229 B2 | 6/2012 | Miller et al. |
| 8,206,409 B2 | 6/2012 | Privitera et al. |
| 8,211,118 B2 | 7/2012 | Catanese et al. |
| 8,216,254 B2 | 7/2012 | McLean et al. |
| 8,235,916 B2 | 8/2012 | Whiting et al. |
| 8,236,016 B2 | 8/2012 | To et al. |
| 8,239,039 B2 | 8/2012 | Zarembo et al. |
| 8,241,272 B2 | 8/2012 | Arnold et al. |
| 8,251,916 B2 | 8/2012 | Speeg et al. |
| 8,252,015 B2 | 8/2012 | Leeflang et al. |
| 8,257,312 B2 | 9/2012 | Duffy |
| 8,260,390 B2 | 9/2012 | Tang |
| 8,272,554 B2 | 9/2012 | Whitman et al. |
| 8,273,078 B2 | 9/2012 | Muenker |
| 8,295,947 B2 | 10/2012 | Lamson et al. |
| 8,303,511 B2 | 11/2012 | Eigler et al. |
| 8,323,240 B2 | 12/2012 | Wulfman et al. |
| 8,323,326 B2 | 12/2012 | Dorn et al. |
| 8,326,437 B2 | 12/2012 | Cully et al. |
| 8,333,740 B2 | 12/2012 | Shippert |
| 8,333,776 B2 | 12/2012 | Cheng et al. |
| 8,337,516 B2 | 12/2012 | Escudero et al. |
| 8,343,167 B2 | 1/2013 | Henson |
| 8,343,187 B2 | 1/2013 | Lamson et al. |
| 8,353,899 B1 | 1/2013 | Wells et al. |
| 8,361,094 B2 | 1/2013 | To et al. |
| 8,361,097 B2 | 1/2013 | Patel et al. |
| 8,364,280 B2 | 1/2013 | Marnfeldt et al. |
| 8,372,098 B2 | 2/2013 | Tran |
| 8,394,110 B2 | 3/2013 | Catanese et al. |
| 8,394,113 B2 | 3/2013 | Wei et al. |
| 8,425,535 B2 | 4/2013 | McLean et al. |
| 8,696,695 B2 | 4/2014 | Patel et al. |
| 8,961,551 B2 | 2/2015 | Taylor |
| 8,979,828 B2 | 3/2015 | Fix |
| 9,005,115 B2 | 4/2015 | Vayser |
| 9,283,040 B2 | 3/2016 | Hendrick et al. |
| 9,603,618 B2 | 3/2017 | Grace et al. |
| 2001/0005789 A1 | 6/2001 | Root et al. |
| 2001/0016717 A1 | 8/2001 | Haarala et al. |
| 2001/0025174 A1 | 9/2001 | Daniel et al. |
| 2001/0031981 A1 | 10/2001 | Evans et al. |
| 2001/0039427 A1 | 11/2001 | Dinger et al. |
| 2001/0041899 A1 | 11/2001 | Foster |
| 2001/0044568 A1 | 11/2001 | Langberg et al. |
| 2002/0002372 A1 | 1/2002 | Jahns et al. |
| 2002/0007190 A1 | 1/2002 | Wulfman et al. |
| 2002/0007204 A1 | 1/2002 | Goode |
| 2002/0010475 A1 | 1/2002 | Lui |
| 2002/0010487 A1 | 1/2002 | Evans et al. |
| 2002/0016628 A1 | 2/2002 | Langberg et al. |
| 2002/0045811 A1 | 4/2002 | Kittrell et al. |
| 2002/0058956 A1 | 5/2002 | Honeycutt et al. |
| 2002/0065543 A1 | 5/2002 | Gomperz et al. |
| 2002/0068954 A1 | 6/2002 | Foster |
| 2002/0087151 A1 | 7/2002 | Mody et al. |
| 2002/0103477 A1 | 8/2002 | Grasso et al. |
| 2002/0103532 A1 | 8/2002 | Langberg et al. |
| 2002/0103533 A1 | 8/2002 | Langberg et al. |
| 2002/0123785 A1 | 9/2002 | Zhang et al. |
| 2002/0151961 A1 | 10/2002 | Lashinski et al. |
| 2002/0183735 A1 | 12/2002 | Edwards et al. |
| 2002/0188278 A1 | 12/2002 | Tockman et al. |
| 2003/0009146 A1 | 1/2003 | Muni et al. |
| 2003/0036788 A1 | 2/2003 | Coe et al. |
| 2003/0050630 A1 | 3/2003 | Mody et al. |
| 2003/0050631 A1 | 3/2003 | Mody et al. |
| 2003/0055444 A1 | 3/2003 | Evans et al. |
| 2003/0055445 A1 | 3/2003 | Evans et al. |
| 2003/0060762 A1 | 3/2003 | Zvuloni et al. |
| 2003/0069575 A1 | 4/2003 | Chin et al. |
| 2003/0073985 A1 | 4/2003 | Mueller et al. |
| 2003/0078562 A1 | 4/2003 | Makower et al. |
| 2003/0105451 A1 | 6/2003 | Westlund et al. |
| 2003/0125619 A1 | 7/2003 | Manning et al. |
| 2003/0167056 A1 | 9/2003 | Jahns et al. |
| 2003/0187460 A1 | 10/2003 | Chin et al. |
| 2003/0187461 A1 | 10/2003 | Chin |
| 2003/0199921 A1 | 10/2003 | Palmer et al. |
| 2003/0204202 A1 | 10/2003 | Palmer et al. |
| 2003/0208209 A1 | 11/2003 | Gambale et al. |
| 2003/0229323 A1 | 12/2003 | Haarala et al. |
| 2003/0229353 A1 | 12/2003 | Cragg |
| 2004/0006358 A1 | 1/2004 | Wulfman et al. |
| 2004/0010248 A1 | 1/2004 | Appling et al. |
| 2004/0015193 A1 | 1/2004 | Lamson et al. |
| 2004/0019359 A1 | 1/2004 | Worley et al. |
| 2004/0039242 A1 | 2/2004 | Tolkoff et al. |
| 2004/0049208 A1 | 3/2004 | Hill et al. |
| 2004/0054368 A1 | 3/2004 | Truckai et al. |
| 2004/0054377 A1 | 3/2004 | Foster et al. |
| 2004/0054388 A1 | 3/2004 | Osypka |
| 2004/0059348 A1 | 3/2004 | Geske et al. |

(56) References Cited

U.S. PATENT DOCUMENTS

| | | |
|---|---|---|
| 2004/0064024 A1 | 4/2004 | Sommer |
| 2004/0068256 A1 | 4/2004 | Rizoiu et al. |
| 2004/0068288 A1 | 4/2004 | Palmer et al. |
| 2004/0093016 A1 | 5/2004 | Root et al. |
| 2004/0097788 A1 | 5/2004 | Mourlas et al. |
| 2004/0102804 A1 | 5/2004 | Chin |
| 2004/0102841 A1 | 5/2004 | Langberg et al. |
| 2004/0111101 A1 | 6/2004 | Chin |
| 2004/0116939 A1 | 6/2004 | Goode |
| 2004/0116992 A1 | 6/2004 | Wardle et al. |
| 2004/0133220 A1 | 7/2004 | Lashinski et al. |
| 2004/0138562 A1 | 7/2004 | Makower et al. |
| 2004/0138744 A1 | 7/2004 | Lashinski et al. |
| 2004/0143284 A1 | 7/2004 | Chin |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0153096 A1 | 8/2004 | Goode et al. |
| 2004/0153098 A1 | 8/2004 | Chin et al. |
| 2004/0153146 A1 | 8/2004 | Lashinski et al. |
| 2004/0172116 A1 | 9/2004 | Seifert et al. |
| 2004/0176840 A1 | 9/2004 | Langberg et al. |
| 2004/0181249 A1 | 9/2004 | Torrance et al. |
| 2004/0216748 A1 | 11/2004 | Chin |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0236397 A1 | 11/2004 | Coe et al. |
| 2004/0243123 A1 | 12/2004 | Grasso et al. |
| 2004/0243162 A1 | 12/2004 | Wulfman et al. |
| 2004/0254534 A1 | 12/2004 | Bjorkman et al. |
| 2004/0260322 A1 | 12/2004 | Rudko et al. |
| 2004/0267276 A1 | 12/2004 | Camino et al. |
| 2004/0267304 A1 | 12/2004 | Zannis et al. |
| 2005/0004644 A1 | 1/2005 | Kelsch et al. |
| 2005/0025798 A1 | 2/2005 | Moulis |
| 2005/0027337 A1 | 2/2005 | Rudko et al. |
| 2005/0038419 A9 | 2/2005 | Arnold et al. |
| 2005/0060030 A1 | 3/2005 | Lashinski et al. |
| 2005/0065561 A1 | 3/2005 | Manning et al. |
| 2005/0090748 A1 | 4/2005 | Makower et al. |
| 2005/0096740 A1 | 5/2005 | Langberg et al. |
| 2005/0106710 A1 | 5/2005 | Friedman et al. |
| 2005/0107667 A1 | 5/2005 | Danitz et al. |
| 2005/0131399 A1 | 6/2005 | Loeb et al. |
| 2005/0149104 A1 | 7/2005 | Leeflang et al. |
| 2005/0149105 A1 | 7/2005 | Leeflang et al. |
| 2005/0197623 A1 | 9/2005 | Leeflang et al. |
| 2005/0222607 A1 | 10/2005 | Palmer et al. |
| 2005/0228402 A1 | 10/2005 | Hofmann |
| 2005/0228452 A1 | 10/2005 | Mourlas et al. |
| 2005/0251116 A1 | 11/2005 | Steinke et al. |
| 2005/0259942 A1 | 11/2005 | Temelkuran et al. |
| 2005/0267557 A1 | 12/2005 | Flynn et al. |
| 2005/0273090 A1 | 12/2005 | Nieman et al. |
| 2005/0283143 A1 | 12/2005 | Rizoiu |
| 2005/0288596 A1 | 12/2005 | Eigler et al. |
| 2005/0288604 A1 | 12/2005 | Eigler et al. |
| 2005/0288654 A1 | 12/2005 | Nieman et al. |
| 2005/0288722 A1 | 12/2005 | Eigler et al. |
| 2006/0041250 A1 | 2/2006 | Poleo |
| 2006/0052660 A1 | 3/2006 | Chin |
| 2006/0084839 A1 | 4/2006 | Mourlas et al. |
| 2006/0100663 A1 | 5/2006 | Palmer et al. |
| 2006/0116746 A1 | 6/2006 | Chin |
| 2006/0116757 A1 | 6/2006 | Lashinski et al. |
| 2006/0149171 A1* | 7/2006 | Vogel .......... A61F 13/069 601/11 |
| 2006/0167417 A1 | 7/2006 | Kratz et al. |
| 2006/0173440 A1 | 8/2006 | Lamson et al. |
| 2006/0217755 A1 | 9/2006 | Eversull et al. |
| 2006/0229490 A1 | 10/2006 | Chin |
| 2006/0235431 A1 | 10/2006 | Goode et al. |
| 2006/0247751 A1 | 11/2006 | Seifert |
| 2006/0253179 A1 | 11/2006 | Goode et al. |
| 2006/0264905 A1* | 11/2006 | Eskridge .......... A61M 25/0021 604/523 |
| 2006/0265042 A1 | 11/2006 | Catanese et al. |
| 2006/0276871 A1 | 12/2006 | Lamson et al. |
| 2006/0287574 A1 | 12/2006 | Chin |
| 2007/0005084 A1 | 1/2007 | Clague et al. |
| 2007/0015964 A1 | 1/2007 | Eversull et al. |
| 2007/0016130 A1 | 1/2007 | Leeflang et al. |
| 2007/0021812 A1 | 1/2007 | Manning et al. |
| 2007/0049929 A1 | 3/2007 | Catanese et al. |
| 2007/0050003 A1 | 3/2007 | Zarembo et al. |
| 2007/0078500 A1 | 4/2007 | Ryan et al. |
| 2007/0083217 A1 | 4/2007 | Eversull et al. |
| 2007/0100211 A1 | 5/2007 | Selover et al. |
| 2007/0100410 A1 | 5/2007 | Lamson et al. |
| 2007/0106328 A1 | 5/2007 | Wardle et al. |
| 2007/0129710 A1 | 6/2007 | Rudko et al. |
| 2007/0142846 A1 | 6/2007 | Catanese et al. |
| 2007/0142880 A1 | 6/2007 | Barnard et al. |
| 2007/0197861 A1 | 8/2007 | Reiley et al. |
| 2007/0198020 A1 | 8/2007 | Reiley et al. |
| 2007/0232981 A1 | 10/2007 | Ravenscroft et al. |
| 2007/0276412 A1 | 11/2007 | Catanese et al. |
| 2007/0282404 A1 | 12/2007 | Cottrell et al. |
| 2007/0293853 A1 | 12/2007 | Truckai et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0009749 A1 | 1/2008 | Delianides et al. |
| 2008/0015625 A1 | 1/2008 | Ventura et al. |
| 2008/0021484 A1 | 1/2008 | Catanese et al. |
| 2008/0021485 A1 | 1/2008 | Catanese et al. |
| 2008/0033232 A1 | 2/2008 | Catanese et al. |
| 2008/0033456 A1 | 2/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039876 A1 | 2/2008 | Catanese et al. |
| 2008/0039889 A1 | 2/2008 | Lamson et al. |
| 2008/0039893 A1 | 2/2008 | McLean et al. |
| 2008/0039894 A1 | 2/2008 | Catanese et al. |
| 2008/0045986 A1 | 2/2008 | To et al. |
| 2008/0051756 A1 | 2/2008 | Makower et al. |
| 2008/0058759 A1 | 3/2008 | Makower et al. |
| 2008/0071341 A1 | 3/2008 | Goode et al. |
| 2008/0071342 A1 | 3/2008 | Goode et al. |
| 2008/0097426 A1 | 4/2008 | Root et al. |
| 2008/0103412 A1 | 5/2008 | Chin |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0125748 A1 | 5/2008 | Patel |
| 2008/0147061 A1 | 6/2008 | Goode et al. |
| 2008/0154293 A1 | 6/2008 | Taylor |
| 2008/0154296 A1 | 6/2008 | Taylor et al. |
| 2008/0161795 A1 | 7/2008 | Wang et al. |
| 2008/0183163 A1 | 7/2008 | Lampropoulos et al. |
| 2008/0208105 A1 | 8/2008 | Zelickson et al. |
| 2008/0221560 A1 | 9/2008 | Arai et al. |
| 2008/0228208 A1 | 9/2008 | Wulfman et al. |
| 2008/0249516 A1 | 10/2008 | Muenker |
| 2008/0262516 A1 | 10/2008 | Gambale et al. |
| 2008/0275497 A1 | 11/2008 | Palmer et al. |
| 2008/0275498 A1 | 11/2008 | Palmer et al. |
| 2008/0281308 A1 | 11/2008 | Neuberger et al. |
| 2008/0287888 A1 | 11/2008 | Ravenscroft |
| 2008/0306333 A1 | 12/2008 | Chin |
| 2009/0012510 A1 | 1/2009 | Bertolero et al. |
| 2009/0018523 A1 | 1/2009 | Lamson et al. |
| 2009/0018553 A1 | 1/2009 | McLean et al. |
| 2009/0034927 A1 | 2/2009 | Temelkuran et al. |
| 2009/0036871 A1 | 2/2009 | Hayase et al. |

(56) References Cited

U.S. PATENT DOCUMENTS

| | | |
|---|---|---|
| 2009/0054918 A1 | 2/2009 | Henson |
| 2009/0060977 A1 | 3/2009 | Lamson et al. |
| 2009/0069761 A1* | 3/2009 | Vogel .................... 604/313 |
| 2009/0071012 A1 | 3/2009 | Shan et al. |
| 2009/0076522 A1 | 3/2009 | Shan |
| 2009/0131907 A1 | 5/2009 | Chin et al. |
| 2009/0157045 A1 | 6/2009 | Haarala et al. |
| 2009/0163899 A1* | 6/2009 | Burton ............... A61B 18/24 606/15 |
| 2009/0192439 A1 | 7/2009 | Lamson et al. |
| 2009/0204128 A1 | 8/2009 | Lamson et al. |
| 2009/0221994 A1 | 9/2009 | Neuberger et al. |
| 2009/0222025 A1 | 9/2009 | Catanese et al. |
| 2009/0227992 A1 | 9/2009 | Nir et al. |
| 2009/0227999 A1 | 9/2009 | Willis et al. |
| 2009/0234378 A1 | 9/2009 | Escudero et al. |
| 2009/0270862 A1 | 10/2009 | Arcenio |
| 2010/0004606 A1 | 1/2010 | Hansen et al. |
| 2010/0016836 A1 | 1/2010 | Makower et al. |
| 2010/0030154 A1 | 2/2010 | Duffy |
| 2010/0030161 A1 | 2/2010 | Duffy |
| 2010/0030262 A1 | 2/2010 | McLean et al. |
| 2010/0030263 A1 | 2/2010 | Cheng et al. |
| 2010/0049225 A1 | 2/2010 | To et al. |
| 2010/0063488 A1 | 3/2010 | Fischer |
| 2010/0125253 A1 | 5/2010 | Olson et al. |
| 2010/0137873 A1 | 6/2010 | Grady et al. |
| 2010/0160952 A1 | 6/2010 | Leeflang et al. |
| 2010/0191165 A1 | 7/2010 | Appling et al. |
| 2010/0191178 A1* | 7/2010 | Ross .................. A61F 9/00736 604/22 |
| 2010/0198194 A1 | 8/2010 | Manning et al. |
| 2010/0198229 A1 | 8/2010 | Olomutzki et al. |
| 2010/0217081 A1 | 8/2010 | Deppmeier et al. |
| 2010/0217277 A1 | 8/2010 | Truong |
| 2010/0222737 A1 | 9/2010 | Arnold et al. |
| 2010/0222787 A1 | 9/2010 | Goode et al. |
| 2010/0240951 A1 | 9/2010 | Catanese et al. |
| 2010/0256616 A1 | 10/2010 | Katoh et al. |
| 2010/0280496 A1 | 11/2010 | Shippert |
| 2010/0324472 A1 | 12/2010 | Wulfman |
| 2010/0331793 A1 | 12/2010 | Tulleken |
| 2011/0004238 A1 | 1/2011 | Palmer et al. |
| 2011/0009942 A1 | 1/2011 | Gregorich et al. |
| 2011/0009957 A1 | 1/2011 | Langberg et al. |
| 2011/0022057 A1 | 1/2011 | Eigler et al. |
| 2011/0028959 A1 | 2/2011 | Chasan |
| 2011/0034790 A1 | 2/2011 | Mourlas et al. |
| 2011/0040238 A1 | 2/2011 | Wulfman et al. |
| 2011/0040312 A1 | 2/2011 | Lamson et al. |
| 2011/0040315 A1 | 2/2011 | To et al. |
| 2011/0040326 A1 | 2/2011 | Wei et al. |
| 2011/0046648 A1 | 2/2011 | Johnston et al. |
| 2011/0054493 A1 | 3/2011 | McLean et al. |
| 2011/0060349 A1 | 3/2011 | Cheng et al. |
| 2011/0071440 A1 | 3/2011 | Torrance et al. |
| 2011/0105947 A1 | 5/2011 | Fritscher-Ravens et al. |
| 2011/0106004 A1 | 5/2011 | Eubanks et al. |
| 2011/0106099 A1 | 5/2011 | Duffy et al. |
| 2011/0112548 A1 | 5/2011 | Fifer et al. |
| 2011/0112562 A1 | 5/2011 | Torrance |
| 2011/0112563 A1 | 5/2011 | To et al. |
| 2011/0112564 A1 | 5/2011 | Wolf |
| 2011/0118660 A1 | 5/2011 | Torrance |
| 2011/0144423 A1 | 6/2011 | Tong et al. |
| 2011/0144425 A1 | 6/2011 | Catanese et al. |
| 2011/0151463 A1 | 6/2011 | Wulfman |
| 2011/0152607 A1 | 6/2011 | Catanese et al. |
| 2011/0152906 A1 | 6/2011 | Escudero et al. |
| 2011/0152907 A1 | 6/2011 | Escudero et al. |
| 2011/0160747 A1 | 6/2011 | McLean et al. |
| 2011/0160748 A1 | 6/2011 | Catanese et al. |
| 2011/0166564 A1 | 7/2011 | Merrick et al. |
| 2011/0178543 A1 | 7/2011 | Chin et al. |
| 2011/0190758 A1 | 8/2011 | Lamson et al. |
| 2011/0196298 A1 | 8/2011 | Anderson et al. |
| 2011/0196355 A1 | 8/2011 | Anderson et al. |
| 2011/0196365 A1 | 8/2011 | Kim et al. |
| 2011/0208207 A1 | 8/2011 | Bowe et al. |
| 2011/0213398 A1 | 9/2011 | Chin et al. |
| 2011/0218528 A1 | 9/2011 | Ogata et al. |
| 2011/0238078 A1 | 9/2011 | Goode et al. |
| 2011/0238102 A1 | 9/2011 | Gutfinger et al. |
| 2011/0245751 A1 | 10/2011 | Hofmann |
| 2011/0257592 A1 | 10/2011 | Ventura et al. |
| 2011/0270169 A1 | 11/2011 | Gardeski et al. |
| 2011/0270170 A1 | 11/2011 | Gardeski et al. |
| 2011/0270289 A1 | 11/2011 | To et al. |
| 2011/0295331 A1 | 12/2011 | Wells et al. |
| 2011/0300010 A1 | 12/2011 | Jarnagin et al. |
| 2011/0301417 A1 | 12/2011 | Mourlas et al. |
| 2011/0301626 A1 | 12/2011 | To et al. |
| 2012/0022512 A1 | 1/2012 | Vaynberg |
| 2012/0029278 A1 | 2/2012 | Sato et al. |
| 2012/0035590 A1 | 2/2012 | Whiting et al. |
| 2012/0041307 A1 | 2/2012 | Patel et al. |
| 2012/0041422 A1 | 2/2012 | Whiting et al. |
| 2012/0053564 A1 | 3/2012 | Ravenscroft |
| 2012/0065659 A1 | 3/2012 | To |
| 2012/0083810 A1 | 4/2012 | Escudero et al. |
| 2012/0083826 A1 | 4/2012 | Chao et al. |
| 2012/0095447 A1 | 4/2012 | Fojtik |
| 2012/0095479 A1 | 4/2012 | Bowe et al. |
| 2012/0097174 A1 | 4/2012 | Spotnitz et al. |
| 2012/0116382 A1 | 5/2012 | Ku et al. |
| 2012/0123411 A1 | 5/2012 | Ibrahim et al. |
| 2012/0136341 A1 | 5/2012 | Appling et al. |
| 2012/0165827 A1 | 6/2012 | Khairkhahan et al. |
| 2012/0165861 A1 | 6/2012 | Palmer et al. |
| 2012/0191015 A1 | 7/2012 | Zannis et al. |
| 2012/0209173 A1 | 8/2012 | Hayase et al. |
| 2012/0215305 A1 | 8/2012 | Le et al. |
| 2012/0220879 A1 | 8/2012 | Fandrey et al. |
| 2012/0239008 A1 | 9/2012 | Fojtik |
| 2012/0245600 A1 | 9/2012 | McLean et al. |
| 2012/0253186 A1 | 10/2012 | Simpson et al. |
| 2012/0253229 A1 | 10/2012 | Cage |
| 2012/0265183 A1 | 10/2012 | Tulleken et al. |
| 2012/0323252 A1 | 12/2012 | Booker |
| 2012/0323253 A1 | 12/2012 | Garai et al. |
| 2012/0330292 A1 | 12/2012 | Shadduck et al. |
| 2013/0006228 A1 | 1/2013 | Johnson et al. |
| 2013/0035676 A1 | 2/2013 | Mitchell et al. |
| 2013/0090563 A1 | 4/2013 | Weber |
| 2013/0096582 A1 | 4/2013 | Cheng et al. |
| 2013/0103047 A1 | 4/2013 | Steingisser et al. |
| 2013/0274614 A1 | 10/2013 | Shimada et al. |
| 2014/0276683 A1 | 9/2014 | Hendrick et al. |
| 2014/0276694 A1 | 9/2014 | Hendrick et al. |
| 2014/0276920 A1 | 9/2014 | Hendrick et al. |
| 2015/0065945 A1 | 3/2015 | Zarins et al. |
| 2015/0272615 A1 | 10/2015 | Newhauser et al. |
| 2016/0001038 A1 | 1/2016 | Romo et al. |
| 2016/0015467 A1 | 1/2016 | Vayser et al. |
| 2016/0120605 A1 | 5/2016 | Hendrick et al. |
| 2016/0256705 A1 | 9/2016 | Webler et al. |

FOREIGN PATENT DOCUMENTS

| | | |
|---|---|---|
| WO | WO 91/17711 | 11/1991 |
| WO | WO 95/33513 | 12/1995 |
| WO | WO 99/07295 | 2/1999 |
| WO | WO 99/49937 | 10/1999 |
| WO | WO 1999058066 | 11/1999 |
| WO | WO 01/076680 | 10/2001 |
| WO | WO 02/49690 | 6/2002 |
| WO | 2003007797 A9 | 5/2004 |
| WO | WO2004049956 | 6/2004 |
| WO | WO2004080345 | 9/2004 |
| WO | WO2004080507 | 9/2004 |
| WO | WO2006/007410 | 1/2006 |
| WO | WO2008005888 | 1/2008 |
| WO | WO2008005891 | 1/2008 |
| WO | WO2008042987 | 4/2008 |

(56) References Cited

FOREIGN PATENT DOCUMENTS

| WO | WO2009005779 | 1/2009 |
|---|---|---|
| WO | WO2009054968 | 4/2009 |
| WO | WO2009065082 | 5/2009 |
| WO | WO2009126309 | 10/2009 |
| WO | WO2011003113 | 1/2011 |
| WO | WO2011084863 | 7/2011 |
| WO | WO2011133941 | 10/2011 |
| WO | WO2011162595 | 12/2011 |
| WO | WO2012009697 | 1/2012 |
| WO | WO2012098335 | 7/2012 |
| WO | WO2012114333 | 8/2012 |
| WO | WO2012177117 | 12/2012 |
| WO | WO2013036588 | 3/2013 |
| WO | 2014151814 A1 | 9/2014 |

OTHER PUBLICATIONS

U.S. Appl. No. 13/800,700, filed Mar. 13, 2013, Hendrick et al.
U.S. Appl. No. 13/800,728, filed Mar. 13, 2013, Hendrick et al.
U.S. Appl. No. 13/828,231, filed Mar. 14, 2013, Bowe et al.
U.S. Appl. No. 13/828,310, filed Mar. 14, 2013, Bowe et al.
U.S. Appl. No. 13/828,383, filed Mar. 14, 2013, Bowe et al.
U.S. Appl. No. 13/828,441, filed Mar. 14, 2013, Bowe et al.
U.S. Appl. No. 13/828,536, filed Mar. 14, 2013, Hendrick et al.
U.S. Appl. No. 13/828,638, filed Mar. 14, 2013, Fiser.
U.S. Appl. No. 13/834,405, filed Mar. 15, 2013, Grace et al.
"Horizon Scanning Technology Prioritising Summary: Laser lead extraction systems," Australia and New Zealand Horizon Scanning Network, Aug. 2010, 15 pages.
Extended European Search Report for European Patent Application No. 07255019.7, dated Oct. 21, 2009, 8 pages.
Official Action for European Patent Application No. 07255019.7, dated Jul. 21, 2010, 4 pages.
Official Action with English translation for Japan Patent Application No. 2007-333173, dated Aug. 13, 2012 7 pages.
Official Action with English translation for Japan Patent Application No. 2007-333173, dated Apr. 30, 2013 5 pages.
Extended European Search Report for European Application No. 07255018.9, dated Nov. 12, 2010, 8 pages.
Official Action for European Patent Application No. 07255018.9, dated Jul. 19, 2011, 3 pages.
Notice of Allowance for European Patent Application No. 07255018.9, dated Jul. 26, 2012 47 pages.
Intent to Grant for European Patent Application No. 07255018.9, dated Nov. 29, 2012, 7 pages.
Decision to Grant for European Patent Application No. 07255018.9, dated Aug. 8, 2013 2 pages.
Official Action with English translation for Japan Patent Application No. 2007-333273, dated Jul. 30, 3012 7 pages.
Official Action with English translation for Japan Patent Application No. 2007-333273, dated Jun. 6, 2013 10 pages.
Notice of Allowance for Japan Patent Application No. 2007-333273, dated Jan. 16, 2014 3 pages.
International Search Report and Written Opinion for International Patent Application No. PCT/US2013/059434, dated Dec. 13, 2013, 14 pages.
Official Action for U.S. Appl. No. 11/615,006, dated Apr. 24, 2009, 11 pages.
Final Action for U.S. Appl. No. 11/615,006, dated Oct. 26, 2009, 9 pages.
Official Action for U.S. Appl. No. 11/615,006, dated Feb. 17, 2010, 8 pages.
Final Action for U.S. Appl. No. 11/615,006, dated Jul. 20, 2010, 9 pages.
Official Action for U.S. Appl. No. 11/615,006, dated Mar. 14, 2013, 16 pages.
Final Action for U.S. Appl. No. 11/615,006, dated Nov. 22, 2013, 16 pages.
Official Action for U.S. Appl. No. 11/615,005, dated Apr. 16, 2009, 13 pages.
Final Action for U.S. Appl. No. 11/615,005, dated Nov. 9, 2009, 10 pages.
Official Action for U.S. Appl. No. 11/615,005, dated Jul. 21, 2010, 10 pages.
Official Action for U.S. Appl. No. 11/615,005, dated Feb. 11, 2011, 12 pages.
Official Action for U.S. Appl. No. 11/615,005, dated Mar. 14, 2013, 16 pages.
Final Action for U.S. Appl. No. 11/615,005, dated Nov. 21, 2013, 20 pages.
Official Action for U.S. Appl. No. 13/800,728, dated Jan. 16, 2014, 14 pages.
International Search Report and Written Opinion issued in PCT/US2014/019258, dated Aug. 8, 2014, 21 pages.
International Search Report and Written Opinion issued in PCT/US2014/021167 dated Jun. 26, 2014, 19 pages.
International Search Report and Written Opinion issued in PCT/US2014/026496 dated Jul. 30, 2014, 16 pages.
International Search Report and Written Opinion issued in PCT/US2015/016899, dated May 1, 2015, 14 pages.
PCT Application No. PCT/US2015/016899 entitled Medical Device for Removing an Implanted Object filed Feb. 20, 2015.
PCT Application No. PCT/US2015/018305 entitled Multiple Configuration Surgical Cutting Device filed Mar. 2, 2015.
U.S. Appl. No. 13/800,651 entitled System and Method of Ablative Cutting and Pulsed Vacuum Aspiration, filed Mar. 13, 2013.
U.S. Appl. No. 14/577,976 entitled Surgical Instrument Including an Inwardly Deflecting Cutting Tip for Removing an Implanted Object filed Dec. 19, 2014.
U.S. Appl. No. 14/589,688 entitled Retractable Separating Systems and Methods filed Jan. 5, 2015.
U.S. Appl. No. 14/627,851 entitled Medical Device for Removing an Implanted Object filed Feb. 20, 2015.
U.S. Appl. No. 14/627,950 entitled Medical Device for Removing an Implanted Object filed Feb. 20, 2015.
U.S. Appl. No. 14/635,742 entitled Multiple Configuration Surgical Cutting Device filed Mar. 2, 2015.
U.S. Appl. No. 61/793,597 entitled Surgical Instrument for Removing an Implanted Object filed Mar. 15, 2013.
U.S. Appl. No. 61/987,993 entitled Dual Mode Mechanical Catheter Cutting System filed May 2, 2014.
U.S. Appl. No. 62/005,315 entitled Surgical Instrument for Removing an Implanted Object filed May 30, 2014.
U.S. Appl. No. 62/058,790 entitled Medical Device for Removing an Implanted Object filed Oct. 2, 2014.
U.S. Appl. No. 62/094,808 entitled Multiple Configuration Surgical Cutting Device filed Dec. 19, 2014.
U.S. Appl. No. 62/113,865 entitled Medical Device for Removing an Implanted Object filed Feb. 9, 2015.
International Preliminary Report on Patentability issued in PCT/US2014/019258, dated Sep. 24, 2014, 12 pages.
U.S. Appl. No. 14/725,766 entitled System and Method of Ablative Cutting and Vacuum Aspiration Through Primary Orifice and Auxiliary Side Port filed May 29, 2015.
U.S. Appl. No. 14/994,921 entitled Device and Method of Ablative Cutting With Helical Tip, filed Jan. 13, 2016.
Extended European Search Report issued in EP147801195., dated Sep. 27, 2016.
U.S. Appl. No. 15/281,981 entitled Laser Ablation Catheter, filed Sep. 30, 2016.

* cited by examiner

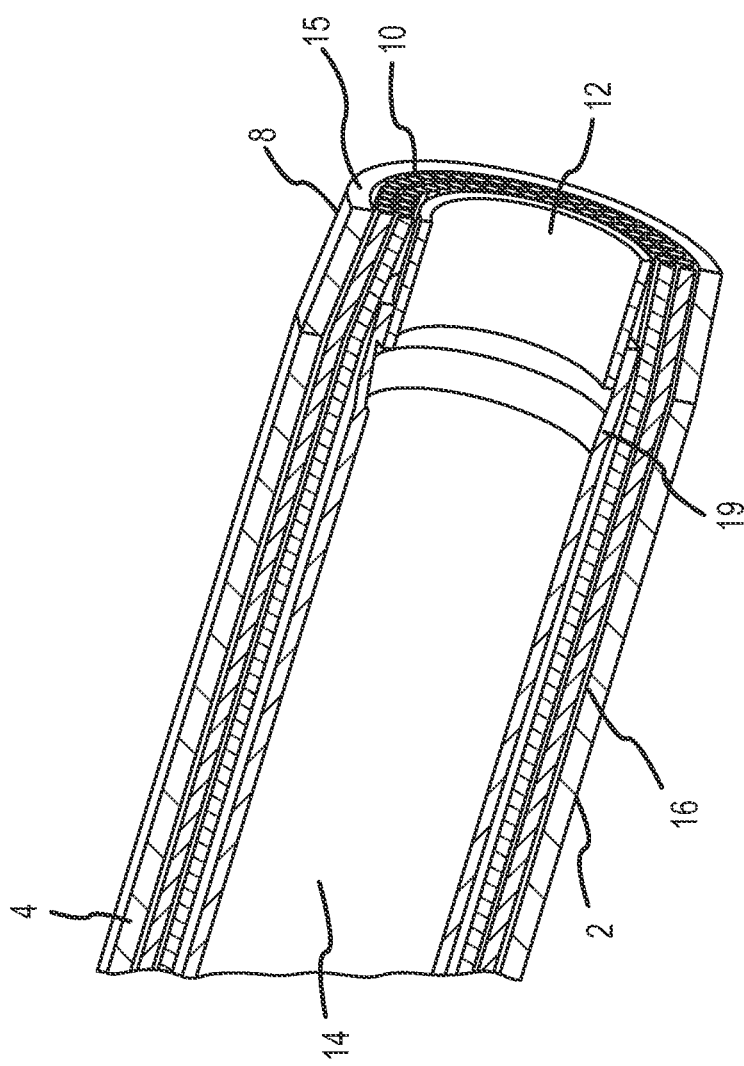

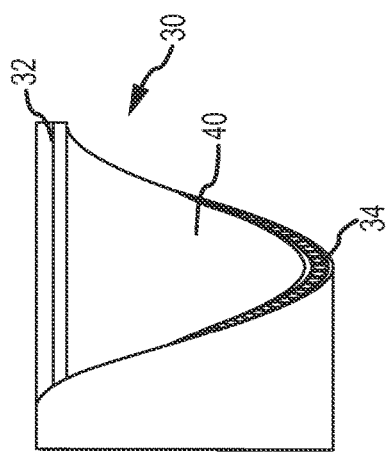
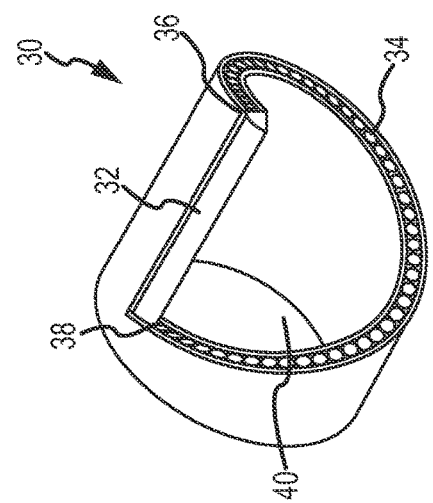
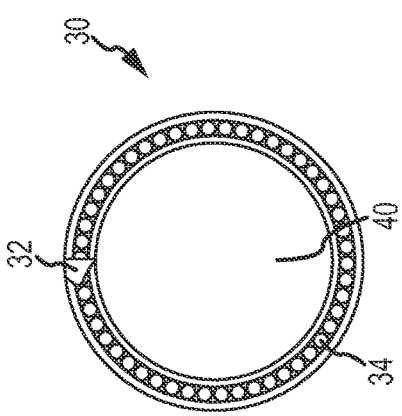

LAST CATHETER WITH HELICAL INTERNAL LUMEN

FIELD

The present disclosure relates generally to medical devices, and, in particular, to a system of improved irrigation and aspiration catheters used in the containment and removal of material resulting from therapeutic treatment of occlusions within blood vessels.

BACKGROUND

Human blood vessels often become occluded or blocked by plaque, thrombi, other deposits, or emboli which reduce the blood carrying capacity of the vessel. Should the blockage occur at a critical place in the circulatory system, serious and permanent injury, and even death, can occur. To prevent this, some form of medical intervention is usually performed when significant occlusion is detected.

Balloon angioplasty and other transluminal medical treatments are well-known and have been proven efficacious in the treatment of stenotic lesions in blood vessels. The application of such medical procedures to certain blood vessels, however, has been limited, due to the risks associated with creation of emboli during the procedure. For example, angioplasty is not the currently preferred treatment for lesions in the carotid artery because of the possibility of dislodging plaque from the lesion, which can enter the various arterial vessels of the brain and cause permanent brain damage. Instead, surgical procedures such as carotid endarterectomy are currently used, wherein the artery is split open and the blockage removed, but these procedures present substantial risks of their own.

Other types of intervention for blocked vessels include atherectomy, deployment of stents, introduction of specific medication by infusion, and bypass surgery. Each of these methods are not without the risk of embolism caused by the dislodgement of the blocking material which then moves downstream. In addition, the size of the vessel may limit access to it.

There is also a need to efficiently remove occlusions from a patient without excess undesired removal of native blood and tissue within the system. Constant flow suction or vacuum pressure is effective at removing freed or dislodged occlusions, but typically remove unnecessary amounts of blood in the process. Thus, there is a need for a system to effectively contain and remove such emboli without undesired consequences, such as excess removal of blood and tissue from the vessel.

Vessels as small as 3 mm in diameter are quite commonly found in the coronary arteries, and even certain saphenous vein graph bypass vessels can also be as small as 3 mm or 4 mm; although some can range as high as 7 mm. Certain of the carotid arteries also can be as small as 4 mm in diameter; although, again, others are larger. Nevertheless, a successful emboli removal system must be effective within extremely small working areas.

Another obstacle is the wide variety in emboli dimensions. Although definitive studies are not available, it is believed that emboli may have approximate diameters ranging anywhere from tens of micrometers to a few hundred micrometers. More specifically, emboli which are considered dangerous to the patient may have diameters as large as 200 to 300 micrometers or even larger. Thus, an effective emboli removal system must be able to accommodate relatively large embolic particles and, at the same time, fit within relatively small vessels.

Another difficulty that must be overcome is the limited amount of time available to perform the emboli removal procedure. That is, in order to contain the emboli produced as a result of intravascular therapy, the vessel must be occluded, meaning that no blood perfuses through the vessel to the end organs. Although certain perfusion systems may exist or may be developed which would occlude emboli while permitting the substantial flow of blood, at present, the emboli may be contained only with a complete occlusion as to both blood flow and emboli escapement. Thus, again depending upon the end organ, the complete procedure, including time for the therapeutic treatment as well as exchanges of angioplastic balloons, stents, and the like, must be completed within a short time. Thus, it may be difficult to include time for emboli removal as well. This is particularly true in the larger size vessels discussed above wherein a larger volume results in additional time required for emboli evacuation.

Additionally, there has been a long felt an unmet need to provide a catheter that is adept at removing harder material, such as calcium (e.g. harder than thrombus and plaque). Cutting and removal of such harder materials generally requires additional procedure time and increased risks.

Moreover, it is important that an emboli containment and removal system be easy to use by physicians, and compatible with present therapeutic devices and methods.

SUMMARY

These and other needs are addressed by the various aspects, embodiments, and configurations of the present disclosure.

In various embodiments, a laser cutting and aspiration atherectomy system is provided, the system comprising a catheter comprising a ring or distribution of fibers that provide a cutting function and an inner lumen through which aspirated material is removed from a patient. It is contemplated that material be removed from the lumen by, for example, a pulsed aspiration system and an in-line filter for material collection as described herein. Embodiments of laser cutting and aspiration atherectomy systems of the present disclosure provide for a wide array of benefits, including providing the ability to create visibly smoother lumens faster than conventional laser ablation methods and systems. Embodiments of the present disclosure ablate less native tissue, separate the lesion from the vasculature in pieces or plugs, and aspirate material through the catheter. With a deflection component, this design can be used to both create a pilot channel and subsequent larger channels, faster than conventional bulk ablation. Devices of the present disclosure create a pilot channel and larger lumens in a faster manner than convention bulk ablation methods and devices.

Embodiments of the present disclosure contemplate various mechanical cutting features provided in combination with a catheter, either in addition to or in lieu of laser ablation means. Such mechanical cutting features include, but are not limited to, various bladed or shearing devices provided at or proximal to a distal end of the catheter. Such mechanical cutting features are contemplated as being substantially fixed to a distal end of a catheter, such as the periphery of an annular distal end, or selectively retractable/extendable from the distal end such that the cutting features are only provided in a position of use when desired. An example of a device that include a mechanical sheath for extending a cutting blade from the distal end of the sheath are described and illustrated in U.S. Pat. No. 5,651,781 to Grace, which is hereby incorporated herein by reference in its entirety for all that it teaches and for all purposes.

In one embodiment, a laser cutting and aspiration atherectomy catheter is provided, the catheter comprising an outer jacket with a tapered outer band, an inner lumen or channel for passage of material, and at least one ring or circular array of cutting fibers. A narrowed orifice or inner band is provided at the distal tip of the catheter. In a preferred embodiment, the catheter comprises a flexible tip with deflection items such as pull wires or shaping wires. Such deflection items are provided in addition to or in lieu of a distal outer jacket. The outer jacket provides a rigid member for communication of various user-applied forces including, but not limited to, torque, compression, and tension forces. The inner lumen provides a reinforced, lubricious lumen for material aspiration. The lumen, in certain embodiments, comprises a coil reinforced polytetrafluoroethylene/polyimide composite. Cutting fibers provide or transmit laser energy for cutting plaque and other occlusive material. In preferred embodiments, the fibers comprise 100 μm fibers provided in concentric arrangements (with respect to one another and/or the catheter).

In various embodiments, one or more catheters of the present disclosure are provided to remove cores or plug-shaped features from an occluded vessel. Devices and methods of the present disclosure contemplate cutting and removing of discrete portions of an occlusions, such as substantially cylindrical portions generally corresponding to the shape/diameter of a catheter distal end and inner lumen. Accordingly, and in contrast with prior art systems and devices, the present disclosure comprises the ability to remove discrete plugs or sections of an occlusion and minimize particulate that may be translocated to different locations within a system and cause additional complications. Annular cutting features, such as ablative lasers and/or mechanical cutting features, inner lumen removal systems, and structural features of catheters that enable application of axial of compression force to the catheter, for example, provide means for extracting discrete plugs or clogs of material from an occlusion and restoration of blood flow through an occlusion.

A method for removing occlusions from a vessel is provided, the method comprising the steps of providing an aspiration catheter comprising: (i) a distal end of substantially annular construction, the substantially annular construction defining an inner lumen for conveyance of material; (ii) at least one cutting element provided coincident or distal with the inner lumen; and (iii) a vacuum pump in fluid communication with the inner lumen and operable to transmit material therethrough; inserting the distal end of the aspiration catheter into a blood vessel navigating the distal end to a site of stenosis, selectively activating appropriate cutting element parameters, activating the vacuum pump, manipulating the aspiration catheter to extract a stenotic material, the stenotic material comprising a cross-sectional substantially the same as a cross-section of the inner lumen, and conveying the stenotic material through the length of the catheter.

The narrowed orifice provides a limiting orifice for material transport and clog resistance and, in certain embodiments, comprises a thin wall, stainless steel hypotube. The outer band provides fiber reinforcement and radio-opacity and, in certain embodiments, comprises a platinum-iridium band.

In one embodiment, a catheter is provided comprising an outer jacket, the outer jacket providing protection for internally-disposed fibers and aiding in maintaining the integrity of the inner lumen(s). The outer jacket further provides enhancements in control of the device, including flexibility of the catheter, track-ability along a path, and enhanced ability to accommodate and/or transmit torque and compression. Preferably, a tricoil arrangement is provided. In alternative embodiments, braided Pebax®, braided polyimide, and Pebax® jackets are provided.

As used herein, a "tricoil" arrangement comprises a shaft comprising coiled wire in a plurality of layers. In certain embodiments, construction of a tricoil includes wrapping at least one round or flat wire in one direction, either clockwise or counter-clockwise around a core mandrel. The wires are wrapped side by side and secured when an appropriate length is achieved. A second layer of at least one round or flat wires is wound in the opposite direction on top of the first layer and secured. The final layer of at least one round or flat wire is wound in the opposite direction of the second layer (or the same direction as the first layer) and secured. The assembly is then welded together at the ends of the shaft to create the component. Wire dimensions and count can be varied in construction for various attributes.

Tricoils contemplated by the present disclosure include, but are not limited to 1-4-4 and 1-6-6 filar count by layer, with flat wires from 0.0014"×0.010" to 0.002"×0.016". Benefits of tricoils include extreme torquability (approaching 1:1 ratio of torque input to torque output, even in bends), kink resistance, inner lumen protection, and durability, to name a few.

Alternative catheter shaft constructions include, but are not limited to Pebax, Braided Pebax, Braided Polyimide, Bicoils, and various combinations thereof.

Inner lumens of catheters of the present disclosure provide a conduit or pathway for aspirating cut or ablated material out of the body. In various embodiments, a vacuum-sealed, lubricious inner surface is provided that does not substantially deform or kink, so as to facilitate consistent removal of material without clogging the device. In certain embodiments, the lumen comprises a coil-reinforced, polytetrafluoroethylene/polyimide composite that provides sufficient hoop strength while allowing for a lubricious inner surface. In additional embodiments, a braid-reinforced PTFE/polyimide composite is provided for the inner lumen. In yet additional embodiments, the inner lumen may have ridges formed in a rifle-like manner to further control the removal of the material.

In certain embodiments, a catheter is provided comprising an internal rifled feature. A catheter jacket is contemplated as comprising an internal feature of a spiral and/or spinning helix or screw configuration. The jacket, which may be a polymer extrusion, comprises a helical rib or rifle such that rotation of the catheter about a longitudinal axis aspirates and/or macerates material. Extension and/or rotation of the catheter induces rotation of the helix structure, thereby freeing material and enabling removal. Freed material may be conveyed from a vessel via a central lumen of the catheter, for example.

The design of the inner lumen is essential to the removal of material without clogging. Requirements for the inner lumen include ovaling/kink resistance, vacuum compression resistance, and inner surface lubricity. Inner lumens that we have tried have been mostly composed of some type of Polyimide construction. We have used pure Polyimide lumens, PTFE/Polyimide Composite lumens, Pure PTFE inner liner with a PTFE/Polyimide composite outer layer.

Reinforcement to the inner lumens has consisted of stainless steel wire braids and coils embedded into the walls of the lumen. These reinforcements prevent kinking, ovaling, and vacuum compression. Inner lumen design could consist of any combinations of components listed in the shaft design section.

Fibers of the present disclosure are provided to deliver laser energy, including that produced by a Spectranetics® CVX-300 and related interface circuit, for example. It is contemplated that fibers of the present disclosure be protected from damage and oriented correctly at the distal tip of the catheter for laser ablation. In various embodiments, approximately fifty to one hundred fibers are provided in concentric annular rings. In a preferred embodiment, seventy four 100 µm fibers are provided in concentric circles. This particular embodiment provides for sufficient energy to ablate tissue, while leaving enough room for a sufficiently large inner lumen space. It will be recognized, however, that the present disclosure is not limited to a particular number or arrangement of fibers. Indeed, various alternative arrangements and quantities of cutting fibers are contemplated as within the scope and spirit of the present disclosure. In alternative embodiments, any combination of fiber size can be utilized, including but not limited to 61/100/130 µm fibers, either in substantially circular or ovoid cross-section.

In various embodiments, a narrowed orifice/inner band is provided that creates a limiting orifice at the distal tip of the catheter. The narrowed orifice helps ensure that if material can pass through it, it will fit down the remainder of the inner lumen. Additionally, the narrowed orifice provides a rigid inner member for fiber support and prevents inner lumen degradation and damage. In one embodiment, a short, thin wall stainless steel hypotube is provided for the narrowed orifice. The shortness of the orifice decreases the chances of clogging at the tip, while the thin wall design reduces the amount of dead space for laser ablation.

In various embodiments, an outer band is provided at the distal end of the catheter, the outer band providing a rigid structure for fiber support and protection as well as ease of manipulation of fiber placement within the distal end. The present disclosure contemplates one or more bands or rows of fibers. One, two, or three or more substantially concentric rows of fibers may be provided for ablating material.

In one embodiment, a Pt/Ir band of approximately 2.0 mm diameter is provided that tapers to approximately 2.3 mm in diameter. Although various embodiments contemplate Pt/Ir bands, any biocompatible material including, but not limited to, stainless steel, plastic, etc. may be used to confine fibers. Outer band embodiments of the present disclosure provide for grouping of at least the distal ends of the fibers proximate an inner band, thus focusing the laser energy and allowing for more of the laser energy to create smaller plugs of material. It is further noted that such embodiments provide for a manufacturing "stop" when the flared inner lumen fits into the preferably tapered portion of the band. Although various embodiments contemplate a tapered outer band, non-tapered bands are also contemplated by the present disclosure.

Catheters of the present disclosure comprise one or more polished surfaces that dictate the interaction of the tip with a surface encountered by the tip. Various embodiments comprise flat polished faces that engage tissue concentrically. Preferably, a flat polish is provided that allows not only the fiber faces to engage tissue at the same time, but also allows the inner lumen to form a vacuum seal on tissue that fills the distal face.

Deflection means are provided in various embodiments of the present disclosure for user-selective manipulation of a distal end of a catheter. In various embodiments, deflection means comprise features involved in offsetting or deflecting the catheter tip, such that a larger lumen may be created in an occlusion, as compared with non-deflective or offset manipulation of the catheter. It is contemplated that deflection means of the present disclosure provide for between approximately 2-5 mm offsets from an initial or aligned positioned, and preferably for between approximately 3-4 mm offsets, particularly for "above the knee" procedures.

In certain embodiments, one or more pullwires are provided as deflection means. Pullwires of the present disclosure comprise wires that run down the length of the catheter and are attached to the distal tip for manipulation thereof. When a tension force is applied to at least one deflection means of such embodiments, the wire(s) causes deflection of the flexible distal end of the catheter. In one embodiment, a wire component is provided in the catheter that is permanently fixed to the distal portion of the catheter. User manipulation of the wire, for example at a user-proximal portion of the catheter, is effective to shape the wire and catheter to a particular desired shape for larger lumen creation. In an additional embodiments, a balloon feature is provided comprising a non-compliant balloon fastened to the distal tip that, when inflated, causes deflection preferentially to one side of a corridor. Additionally, ramped features, such as those shown an described in U.S. Pat. No. 5,484,433 to Taylor et al., which is hereby incorporated by reference in its entirety may be included within catheters of the present disclosure.

Embodiments of the present disclosure also contemplate a flexible tip provided in combination with deflection means such as a shaping spine or pullwire. A flexible portion at the distal tip allows for bends and angled to be induced at the intended site, while the rest of the catheter can remain straight and rigid. In certain embodiments, laser cut hypotubes are provided having a thick enough wall for flexing without buckling and kerf widths (laser cut widths) large enough to allow for the bend angle required. Such tips are attached to the end of the catheter by laser welding (with a tricoil) or a fuse joint (plastics) and can be cut to preferentially bend a certain direction. Additionally, Pebax segments may be provided, such segments being fused to the end of a tricoil and able to deflect using a pullwire and/or shaping wire. Employing polymer tubing, a wire coil, or a combination thereof for the distal body, a guide wire may be used in peripheral or coronary angioplasty applications.

Various embodiments of the present disclosure also contemplate a spiraled ring ablation device with a mechanical cutting tip at the distal end of the catheter. A laser fiber ring is provided for cutting tissue while a blade or mechanical cutting edge assists in cutting and removal of harder calcium deposits, for example. The distal end may also be rotatable at various speeds to create various motions with the mechanical cutting edge. The edges of a spiral band may further be provided with mechanical cutting features. Thus, in various embodiments, a catheter is provided with a combination of laser and mechanical cutting or ablation features. Cutting efficiencies, particular with respect to calcium deposits, are thus improved.

Concurrent extension and rotation of at least a distal end of a catheter of the present disclosure is provided as a means for cutting and ablating an obstruction. In one embodiment, a method of removing material from a blood vessel is contemplated, the method comprising the step of concurrently extending a catheter along a length of a vessel and rotating at least the distal end of the catheter. Such methods provide various advantages, including the ability to core out or extract a substantially cylindrical mass of material and providing a fluid flow corridor through an obstruction, thus enabling fluid/blood flow through the corridor even when complete removal or ablation of the obstruction is not performed.

Various embodiments of the present disclosure contemplate a pulsed vacuum aspiration system to evacuate material removed during an atherectomy procedure and remove material as it is ablated and moved down the shaft of a vacuum device in a pulsed manner.

Although pulsed aspiration systems are contemplated with various features shown and described herein, the features, systems and methods described herein are not limited to use with pulsed aspiration systems and methods. Indeed, various removal means, devices and methods are contemplated for use with various features of the present disclosure. Such means, devices and methods include, but are not limited to, spinning helixes, rotating screws, Archimedes screws, continuous vacuum aspiration, and various combinations thereof. Additionally, aspiration systems other than a pulsed aspiration systems may be used. For example, an additional embodiment may include the use of a peristaltic pump for material aspiration in conjunction with laser cutting and coring. Use of the peristaltic pump may negate the use of a solenoid valve or pulse width modulator, due to the nature of peristaltic pump material movement. The peristaltic pump embodiment differs mainly from the vacuum pump embodiment in that it relies on a liquid filled system to aspirate or move material, while the vacuum pump system utilizes both air and liquid filled system, leading to potential variability within the system due to the compressibility nature of air. With reference to FIG. 4, if a peristaltic pump is used, then the vacuum pump 18 would be replaced with a peristaltic pump and the solenoid valve 22 and pulse width modulator 20 would be deleted.

Other disclosures include using mechanical or laser means to macerate/destroy material as it enters the inner lumen.

In various embodiments, one or more vacuum pumps are provided to generate the vacuum required to aspirate material down a central lumen of a catheter. Vacuum levels in the range of 10 to 30 in-Hg, and preferably approximately 20 in-Hg, are provided. Vacuum pumps of the present disclosure preferably comprise a disposable collection container.

Another aspect of the present disclosure comprises a clogging detection means which detects clogging in an aspiration tube or an aspiration catheter during an aspiration operation.

In certain embodiments, an aspirator includes clogging detection means for measuring a change in a flow rate of an aspirate at one more points in a system. Alternatively, clogging detection means comprise means for measuring a change in a weight of an aspirate sampling bottle and/or a change in an amount of aspiration dropping in an aspirate sampling bottle. In various embodiments, clogging alert means for informing a user that clogging in the aspiration tube or the aspiration catheter has occurred are provided.

Clogging alert means of the present disclosure include, but are not limited to warning sounds and/or visual indicators that immediately notify a user of a potential clog such that remedial action can be taken immediately.

In one embodiment, an aspirator is provided with clogging detection means, the clogging detection means comprising a load cell for measuring the weight of an aspirate collection feature, such as a sampling jar. When clogging in the aspiration catheter or the aspiration tube occurs, a rate of increase in the weight of the collection features decreases. Therefore, clogging in the aspiration catheter or the aspiration tube can be detected by measuring a change in weight of the aspirate collection feature with the load cell. Where clogging is detected, a warning indicia is provided to inform an operator that the clogging has potentially occurred.

In alternative embodiments, detection of clogging is performed by measuring a change in a flow rate of an aspirate at one or more points in the system, such as blood flow in the aspiration catheter and/or the aspiration tube. For example, flow rate in a part of an aspiration tube immediately before an aspirate collection device is continuously measured by a flowmeter, an ultrasonic wave flowmeter, or the like during an aspiration operation. When a flow rate falls to a set value or less, it can be judged that clogging has occurred.

In still further embodiments, clogging or blockage is detected based on monitoring pressure values at one or more points in a system. Since an aspiration pressure increases when the aspiration catheter or the aspiration tube is blocked, when the aspiration pressure rises to a set value or more, it can be judged that clogging has occurred. It is also possible to set a threshold value for an output to the pressure indicator and emit a warning when the output increases to the threshold value or more.

When clogging in the aspiration catheter or the aspiration tube has occurred, it is preferable that an operator is informed to that effect immediately, and prompt measures for restart of aspiration are taken. Examples of the clogging alert means emitting a warning indicia include, but are not limited to a buzzer, a bell, various electronic sounds, and artificial voices. The clogging alert means is not specifically limited. If the alert means using a warning sound is adopted, an operator can concentrate on manipulation sufficiently and safety of an operation or a patient is remarkably improved because it is unnecessary for the operator to look at the medical aspirator in order to monitor clogging during the manipulation. Clogging alert means are further contemplated as comprising visual indicia, including various lamps, LEDs, or the like.

Embodiments of the present disclosure contemplate a vacuum system with clog detection features. Such embodiments comprise means to detect a difference in vacuum pressure, such as when a clog or obstruction is provided in a vacuum line and means to alert a user or operator of the device. Alert means of the present disclosure include, but are not limited to, auditory and visual feedback features to identify to the user that a clog in the vacuum system is present or likely present.

In one embodiment, alert means comprise a mechanical switch or feature that is activated upon a pressure value in a vacuum system exceeding a predetermined value. For example, a weighted or pressurized element is provided in a manner wherein the element is substantially hidden from a user's view when the vacuum is operating under normal unobstructed conditions. However, upon the pressure value exceeding a predetermined value, such as that corresponding to a significant blockage in the vacuum system, the element is displaced to a position whereby it is visible to a user. Such an embodiment provides a "red flag" warning indicia to a user that the vacuum is not operating normally and an obstruction may be present.

In a further embodiment, alert means comprise audio and/or visual indicia prompted by a waveform output of vacuum pressure at a particular point in the system. For example, a vacuum system is provided with one or more electromechanical pressure sensing features, such features outputting a waveform corresponding to pressure values at one or more points over time. Where at least one of such pressure values exceeds (thus indicating an upstream blockage) or drops below (thus indicating a downstream blockage) a predetermined value, the detected value prompts an associated audio and/or visual alarm to indicate to a user the presence of one or more blockages.

A method of operating a vacuum assisted aspiration system is provided, the method comprising the steps of: prepping and priming a catheter for surgery, inserting the catheter into a patient via a sheath, navigating the catheter to a site of stenosis (e.g. via guidewire), selecting appropriate mechanical and/or laser cutting parameters, activating appropriate mechanical and/or laser cutting features, activating a pulsed aspiration system via a foot pedal or similar user-actuation means, manipulating the catheter to core out stenotic material, applying laser energy and/or mechanical means to core material, and transmitting material into a distal tip of the catheter and subsequently conveying the material through the length of the catheter. A user may subsequently repeat various aforementioned steps until a stenosis is adequately removed or remedied. In embodiments comprising clog detection means, wherein a lesion material becomes clogged within the system, vacuum pressure will increase at a point in the system. Wherein such a condition occurs, alert means indicate to a user the presence of a clog. The user may then take correction, such as removing the device from the patient, purging the catheter, and subsequently re-employing the device for subsequent operations.

In one embodiment, a custom vacuum pump is provided. Alternatively, known and/or commercially available pumps, such as personal patient pumps are provided. It will be recognized that the present disclosure is not limited to any specific pump size, power, displacement etc. Preferably, however, one or more pumps of small, lightweight design that can still create and maintain the required vacuum levels are provided.

Various vacuum systems of the present disclosure comprise one or more solenoid valves to open and close a line between the vacuum pump and the aspiration lumen of the catheter. Such valves are compatible with blood, are liquid sealed, and have a fast response time for opening and closing at high frequencies.

In various embodiments, a custom valve is provided that is small, fast responding and can be fully integrated with the pump and other circuitry. The valve(s) may be disposable with the rest of the system or reusable (e.g. with the proper filters).

One or more filters are provided to collect material being aspirated down the inner lumen of the catheter. Filters of the present disclosure are provided with, for example, Luer valve fittings for ease of use, removal, cleaning, and reattachment. One filter of the present disclosure comprises Luer valve sides of two syringes with a plastic grate inside. The pore size of the grate is large enough to let liquid move through unimpeded, but small enough to prevent material from going through the valve into the disposable collection jar.

Pulsed vacuum systems of the present disclosure comprise a pulse width modulator to provide various signals to a valve, causing the valve to react faster/slower and remain open/closed for longer amounts of time.

Pulsing characteristics can be programmed into the vacuum pump/valve, and/or controlled by a user-operable feature such as a manual device or foot-pedal. In certain embodiments, a delay is built into an interface circuit of the present disclosure, the delay provided to allow the vacuum pump to run for a set amount of time after cutting operations have ceased, thereby allowing the inner lumen and other aspiration corridors to clear of material, thus reducing risk of back-flow and providing the benefit of generally clearing or purging the system. The delay may be programmed to allow the vacuum to run various durations. It will be recognized, however, that a preferred duration is one that accounts for length of lumen/corridor and flow rate and thus provides sufficient clearing of the system.

Preferably, a preset/adjustable custom circuit is provided, the custom circuit designed for pulsed aspiration in combination with additional features. The circuit comprises a user interface for adjustment, or is alternatively completely preset. In one embodiment, an interface circuit is provided that interfaces with a laser excimer system foot pedal, such as that associated with the Spectranetics® CVX-300, allowing for activation of the pulsed aspiration system only when lasing is actively occurring, thus further reducing the amount of undesired or unnecessary fluid transferred from a patient. A delay is built into the circuit to allow the vacuum pump/valve to run for a set amount of time after lasing so that the inner lumen can clear material. Such a delay may be pre-programmed based on various system characteristics including, but not limited to, the length of the inner lumen.

The present disclosure can provide a number of advantages depending on the particular configuration. Advantages of embodiments of the present disclosure include, but are not limited to, the evacuation of particulate and occlusions from an atherectomy site as such particulate is generate, thus reducing the risk of mere translocation of the particulate to other areas of the circulatory system. Various embodiments of the present disclosure contemplate user-selected pulsation of a vacuum or removal system such that the system may be pulsed only as particulate generation is occurring, decreasing the volume of blood or fluid extracted from a patient.

Additionally, pulsation features of the present disclosure are capable of providing short duration peak vacuum pressures that enhance the device's ability to evacuate larger or higher friction particles. Pulsed action methods and devices create a stepped motion from the extraction site down a catheter shaft, for example. Pulse width and duty cycle of the vacuum pulse can be varied to optimize the particle aspiration process for highest efficiency and minimum blood and fluid removal.

In various embodiments, the device of the present disclosure may not only be used for dissecting, coring and aspirating plug-type portions of lesion material, but the device or embodiments of the device of the present disclosure may be used to perform bulk ablation. Bulk ablation generally encompasses the use of catheter having a full face of laser emitters at its distal end, and all of the lesion material contacted by the energy transmitted by the laser emitters is ablated, in comparison to ablating the lesion with a circular or helical arrangement of lasers and coring the tissue. Depending upon the size and type of lesion, the bulk ablation technique may potentially increase the efficiency of the system and removal of debris. Such a technique may be used by a user/physician based on the specific removal needs and may comprise, for example, inserting an additional laser catheter through a central lumen to provide a substantially flat laser ablation distal end of the catheter.

Various embodiments of the present disclosure contemplate mechanical material removal means, such as helixes and screws. In one embodiment, a method and system is provided comprising a stainless steel hypotube further comprising a helical structure, the helical structure is capable of rotation at, for example, at approximately 15,000 to approximately 100,000 RPM. Such helical structure(s) are capable of macerating and translating material along their length, and thus removing occlusions from a vessel. Helical structures of the present disclosure may be provided in combination with various vacuum systems, laser and mechanical ablation systems, and other features described herein to assist in removal of material.

In various embodiments, a system is provided with user-selected presets for pulsed vacuum aspiration modes. For example, in one embodiment, a plurality of settings are provided in connection with a pulse width modular such that a user/physician may select between general vacuum aspiration settings including "low," "medium," and "high" based on the user's first-hand knowledge of the amount of particulate being evacuated or desired to be evacuated.

In various embodiments, one or more filters are applied, such as catch filters that allow a physician to visualize and/or analyze material being removed from an aspiration site.

These and other advantages will be apparent from the disclosure of the aspects, embodiments, and configurations contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

The term "computer-readable medium" as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is always equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

The terms "determine", "calculate" and "compute," and variations thereof, as used herein, are used interchangeably and include any type of methodology, process, mathematical operation or technique.

A "laser emitter" refers to an end portion of a fiber or an optical component that emits laser light from a distal end of the catheter towards a desired target, which is typically tissue.

An optical fiber (or laser active fibre) is a flexible, transparent fiber made of an optically transmissive material, such as glass (silica) or plastic, that functions as a waveguide, or "light pipe", to transmit light between the two ends of the fiber.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 3 is cross-sectional view of a distal end of a catheter according to one embodiment of the present disclosure;

FIG. 5 is a perspective view of a distal end of a catheter according to one embodiment of the present disclosure;

FIG. 6 is an elevation view of a distal end of a catheter according to one embodiment of the present disclosure;

FIG. 7 is an elevation view of a distal end of a catheter according to one embodiment of the present disclosure;

DETAILED DESCRIPTION

Although a large portion of this disclosure includes a discussion of laser catheters (or catheters having a combination of laser emitters and mechanical cutting tips at the distal end its distal end) used in conjunction with an aspiration system, catheters having mechanical cutting tips may also be used. Laser catheters typically transmit laser energy through optical fibers housed in a relatively flexible tubular catheter inserted into a body lumen, such as a blood vessel, ureter, fallopian tube, cerebral artery and the like to remove obstructions in the lumen. Catheters used for laser angioplasty and other procedures may have a central passageway or tube which receives a guide wire inserted into the body lumen (e.g., vascular system) prior to catheter introduction. The guide wire facilitates the advancement and placement of the catheter to the selected portion(s) of the body lumen for laser ablation of tissue.

Examples of laser catheters or laser sheaths are sold by the Spectranetics Corporation under the tradenames ELCA™ and Turbo Elite™ (each of which is used for coronary intervention or catheterization such as recanalizing occluded arteries, changing lesion morphology, and facilitating stent placement) and SLSII™ and GlideLight™ (which is used for surgically implanted lead removal). The working (distal) end of a laser catheter typically has a plurality of laser emitters that emit energy and ablate the targeted tissue. The opposite (proximal) end of a laser catheter typically has a fiber optic coupler, which connects to a laser system or generator. One such example of a laser system is the CVX-300 Excimer Laser System, which is also sold by the Spectranetics Corporation.

Figure 2:
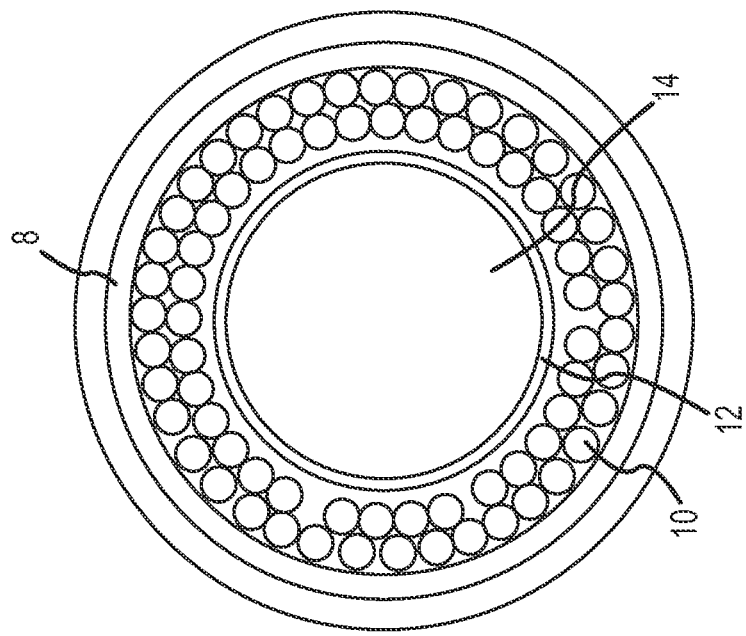
FIG. 2 is an elevation view of a distal end of a catheter according to one embodiment of the present disclosure.
Figure 1:
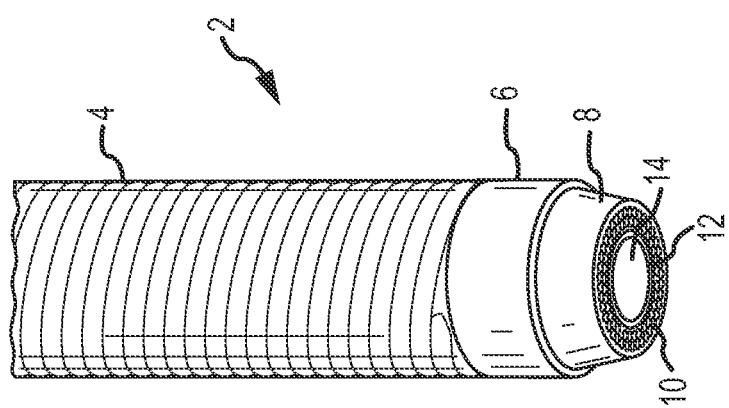
FIG. 1 is a top perspective view of a distal end of a catheter according to one embodiment of the present disclosure.

Referring now to FIGS. 1-2, a distal end of a laser catheter 2 for atherectomy procedures in accordance with one embodiment of the present disclosure is shown. The laser catheter 2 may (as depicted in FIGS. 1 and 2) or may not include a lumen 14. If a lumen 14 is included in the laser catheter 2, a clinician may slide the laser catheter over a guidewire (not shown) through lumen 14. It may, however, be preferable for the catheter to have a separate guidewire lumen located between the inner band and outer jacket. Incorporation of such a guidewire lumen is generally known to one of ordinary skill in the art, and all such guidewire lumens are within the knowledge of one skilled in the art are considered within the scope of this disclosure.

As shown, the catheter 2 comprises an outer jacket 4 or sleeve. The outer jacket 4 comprises a flexible assembly with the ability to resist user-applied forces such as torque, tension, and compression. The proximal end (not shown) of the catheter 2 is attached to a fiber optic coupler (not shown) and includes an outer jacket, inner band and a plurality of optical fibers similar to the configuration and orientation of such components depicted in FIGS. 1 and 2. The distal end 6 of the catheter 2 comprises a tapered outer band 8, which is attached to the distal end of the outer jacket 4, a plurality of optical fibers 10 acting as laser emitters, inner band 12 creating an orifice that provides an entrance to an inner lumen 14 that is connected to an aspiration system discussed in more detail below. The energy emitted by the laser emitters 10 cuts, separates, and/or ablates the scar tissue, plaque build-up, calcium deposits and other types of undesirable lesion or bodily material within the subject's vascular system in a pattern substantially similar to that of the cross sectional configuration of the laser emitters 10.

The cutting means in this embodiment is a laser ablation means that includes laser emitters 10 embedded within a catheter 2 comprising a lumen 14. In this particular embodiment, approximately seventy-four laser emitters 10 are provided in a generally concentric configuration. Also provided substantially concentric with and interior to the laser emitters 10 (and optical fibers) is an inner lumen 14, which provides a potential conduit or passageway for translocation of materials cut or ablated by the laser emitters 10.

As the energy emitted by the laser emitters 10 contacts the undesirable bodily material within the subject's vascular system, it separates and cuts such material in a generally concentric configuration. In other words, one of ordinary skill in the art may refer to this technique as coring. And if the bodily material that is cut is substantially solid, it will appear as generally cylindrically looking core or plug. Although FIGS. 1-2 illustrate the laser emitters 10 in a generally concentric configuration, those skilled in the art will appreciate that there are numerous other ways and configurations in which to arrange a plurality of laser emitters. Additionally, although these two figures illustrate an outer jacket 4 and an inner band 12, those of skill in the art will appreciate that distinct components need not be used, and the optical fibers may be encapsulated within a single sleeve having a lumen. Accordingly, FIGS. 1-2, as well as FIG. 3 discussed below, are not intended to represent the only way that a laser catheter may be configured and constructed, and all such configurations and constructions are within the knowledge of one skilled in the art are considered within the scope of this disclosure.

FIG. 3 is a cross-sectional perspective view of a laser catheter according to one embodiment of the present disclosure. A flexible distal tip 2 is provided, the distal tip 2 comprising a central or inner lumen 14 provided substantially concentric with one or more annular arrays of optical fibers 10 and an outer jacket 4. An inner band 12 is provided at a far distal end of the tip 2. In the depicted embodiment, the inner band 12 has an orifice comprising an internal diameter that is smaller than a minimum internal diameter of the inner lumen 14. The smaller size of orifice of the inner band 12 (either alone or in conjunction with the location and configuration of the laser emitters 10), in comparison to the size of the lumen 14, ensures that the material will have a smaller cross section than that of the lumen 14, thereby reducing the likelihood that the bodily material will become trapped or clogged in the lumen 14 as it is aspirated therethrough. Although FIG. 3 depicts the orifice of the inner band 12 as being less than the minimal internal diameter of the inner lumen 14, the orifice of the inner band 12 may be equal to or greater than the minimal internal diameter of the inner lumen 14.

The inner band 12 comprises a proximal end, a distal end, an interior surface and an exterior surface. When placed within the catheter 2, the distal end of the inner band 12 is substantially aligned or flush with the far distal end of the tip 15. The inner band 12 may be attached to the catheter via numerous means known to one of ordinary skill in the art. For example, the dimension of the exterior diameter (or circumference) of the inner band 12 may be slightly greater than the diameter (or circumference) of the lumen at the distal tip of the catheter such that the inner band is press fit into the distal tip of the catheter 2. Additionally, the inner band 12 may be attached to the lumen by various known adhesives.

The interior surface of the inner band 12 may be straight or tapered. That is the interior diameters of the inner band may be the same or different (e.g., smaller or larger) in comparison to one another. For example, the interior surface of the inner band 12 may be tapered such that the interior diameter at its proximal end is greater than the interior diameter at its distal end.

Upon installation of the inner band 12 into the distal tip of the catheter, the interior surface of the proximal end of the inner band 12 may or may not be aligned or be flush with the surface of the lumen. Regardless of the alignment of the two surfaces, the lumen 14 may include a transition portion that is tapered from the point at which the proximal end of the inner band 12 contacts the lumen until a predetermined point located proximally thereof. The taper may either an increasing or decreasing taper as the lumen transitions proximally of the inner band 12. The tapered portion may also extend distally beyond the proximal end of the inner band 12 and be used to affix the inner band 12 within the catheter. For example, as depicted in FIG. 3, a portion of the inner lumen 14 may comprise a tapered portion 19 to receive and envelope a proximal portion of the inner band 12. The inner band 12 may also provide structural support to the distal end of the catheter, and particularly to the distal ends of the fibers 10, which are surrounded at an outer diameter by a tapered outer band 8.

Outer band 8 is tapered from its proximal end to its distal end 2, thereby facilitating the ease of movement of the catheter within a blood vessel. The outer band 8 abuts outer jacket 4, and in order to further facilitate movement of the catheter within the blood vessel, it may be preferable that the exteriors of the outer band 8 and outer jacket 4 be aligned.

The catheter comprises a flexible distal end 2, the flexible distal end 2 being operable by a user. The position of the distal end is controlled by one or more deflection means 16 which may include, but are not limited to, pullwires, shaping wires, and similar force-transmitting features controlled by a user at a user-proximal location of the device. Actuation of at least one deflection means 16 applies force to the distal tip 2, thus deflecting the distal tip 2 from a longitudinal axis of the remainder of the catheter device. The deflection means allows the clinician to both create a pilot channel and subsequent larger channels, faster than conventional bulk ablation. For example, the clinician initially cuts the bodily material within the vascular system without deflecting the distal end of the catheter. Then, the clinician deflects the distal end of the catheter using the deflection means and subsequently cuts additional bodily material at the same general location within the subject's vascular system, thereby creating a larger channel therethrough in comparison the channel created initially created.

Figure 4:
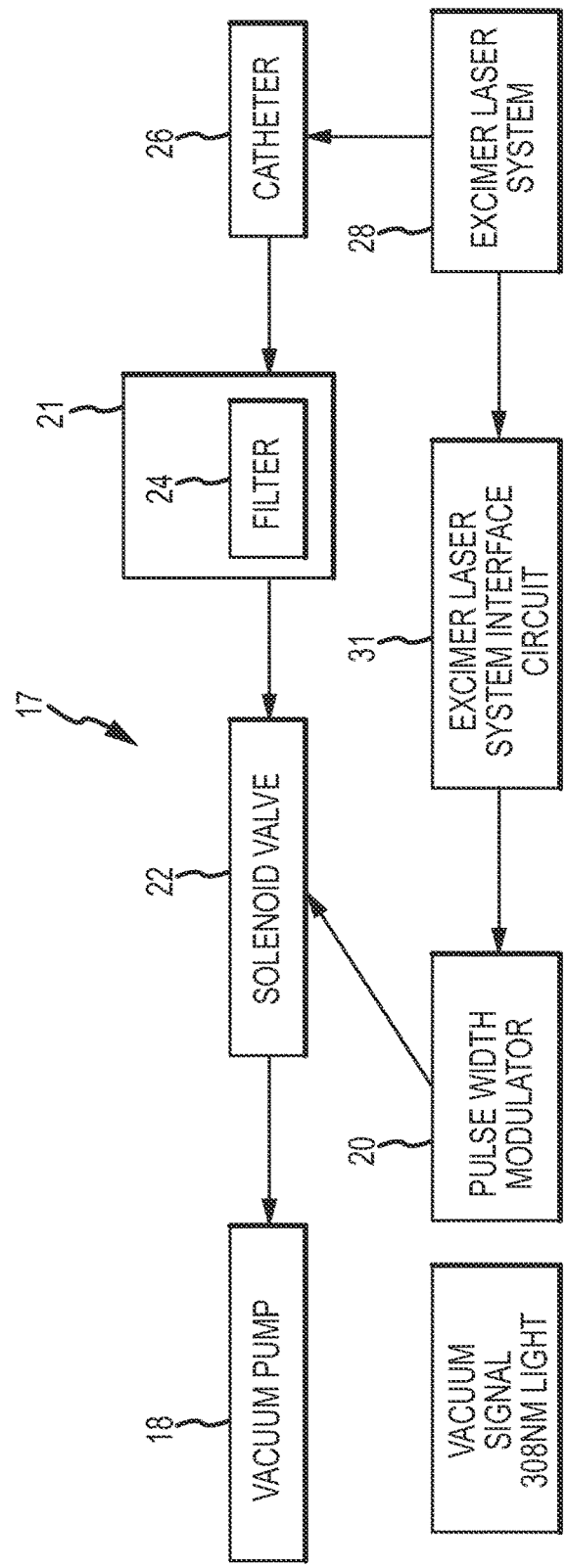
FIG. 4 is a schematic of a pulsed vacuum system according to one embodiment of the present disclosure.

FIG. 4 is a schematic depicting a pulsed aspiration system 17 according to one embodiment of the present disclosure that may be connected to the lumen of the catheter to evacuate the ablated or cored bodily material from a subject's vascular system using various embodiments of a catheter comprising a distal tip having laser cutting means and/or mechanical cutting means. As shown, a vacuum pump 18 is provided, the vacuum pump 18 being interconnected to a pulse width modulator 20 in operative communication with at least one solenoid valve 22, the actuation of which creates one or more pressure differentials to the aspiration system. Accordingly, rather than creating a constant suction pressure within the lumen of a catheter to evacuate cut and/or ablated bodily material from a subject's vascular system, the aspiration system of the present disclosure applies alternative pressure(s), thereby creating pulses of suction pressure within the lumen. Utilizing a series of constant and/or varying pressure pulses is potentially beneficial in aspirating bodily material, particularly when aspirating larger cylindrically looking core or plug like shapes of bodily material.

A filter 24 is provided upstream of the solenoid valve 22, the filter 24 provided for filtering debris and aspirated bodily material and also for providing visual feedback to a user related to the type, quantity, and flow rate of material being removed from a patient. Fluid and material is provided to the filter 24 via a catheter 26 interconnected to, for example, an excimer laser system 28 for the treatment of peripheral and coronary arterial disease such as the CVX-300 Excimer Laser System sold by the Spectranetics Corporation.

In various embodiments, a fluid collection jar 21 may also be provided in fluid communications with the vacuum pump 18. The fluid collection container 21, such as a jar, comprises one or more known devices for collecting and filtering fluid removed from a patient. The container 21 preferably comprises transparent sidewalls for providing visual feedback to a user regarding flow-rate, content, coloration, etc. Filter means are also provided for removing particulate from liquids. Those of skill in the art will appreciate that various types of fluid collection containers may be used. The fluid collection container 21 and/or filter 24 may also comprise one or more custom filter features with various mesh sizes, capacities, etc. based on the specific application.

Pulse width modulator(s) 20 of the present disclosure provides for automatic control and varied application of vacuum pressure to the remainder of the aspiration system, including features and devices of an excimer laser system 28 provided in communication with the aspiration system 17. It will be recognized that where an excimer laser system 28 is provided for cutting and ablating debris and particulate from a blood vessel of a patient, efficient removal of such debris is still required. The present disclosure provides an aspiration system 17 for use with an excimer laser cutting system 28 wherein blood and debris may be aspirated or removed in a pulsed fashion, thereby minimizing the amount of clean or healthy blood that is unnecessarily removed from a patient.

A pulse width modulator 20 is provided as a control means or controller for controlling the opening and closing of at least one solenoid valve 22, the solenoid valve 22 provided for selective application and segregation of a vacuum pressure provided by the vacuum pump 18 from the remainder of a system. Controlling the frequency and duty cycle at which the solenoid valve 22 opens and closes influences the pulse pattern, such as the pulse frequency, the pulse width, the pulse pressure, the rate at which the pulse pressure increases and/or decreases, etc. The settings for the pulse width modulator 20 may be manually adjusted by a user to provide a desired pulse pattern or the settings may be automatically adjusted by parameters stored within computer-readable medium controlled by a central processing unit "CPU". For example, during portions of a procedure where relatively little particulate is being ablated or cut from a patient's vascular system, the pulse width modulator 20 may be manipulated such that applications of vacuum forces are relatively far apart, thus removing a minimal amount of blood and fluid from a patient when such removal is not necessary. Alternatively, where significant amounts of particulate are being ablated and removed from a patient, the pulse width modulator may be manipulated or programmed to provide frequent constant and/or varying vacuum pulses and remove greater amounts of fluid from the patient.

The filter 24 preferably comprises a transparent device such that a user is provided with some level of visual feedback as to how much plaque or particulate is being removed from a patient. Based on this feedback, for example, a user can selectively manipulate the settings of the pulse width modulator 20 to alter the overall flow rate of material from a patient. In various embodiments, the pulse width modulator 20 and/or solenoid valve 22 settings are controlled by a foot pedal, hand switch, or similar user-actuatable device.

The filter 24, vacuum pump 18, flow sensor(s) (not shown) and/or pressure sensor(s) (not shown) may output signals that are transmitted to the CPU controlling the pulse width modulator 20. The computer-readable medium may include an algorithm, which receives the output signals and instructs the CPU how to adjusts the parameters at which the solenoid valve opens and closes.

An interface circuit 31 may also be provided for communication with the pulse-width modulator 20. The interface circuit is provided to communicate with, for example, the excimer laser system 28. The computer readable medium and CPU discussed above may be located in the excimer laser system 28. In addition to controlling the solenoid valve, the excimer laser system may also provide for a clogged aspiration detection system and control for a conduit-clearing mode based on various additional system parameters, including laser cutting operations.

FIG. 5 is a perspective view of a distal tip 30 of a catheter according to one embodiment of the present disclosure. FIG. 6 is a side elevation view thereof. FIG. 7 is a front elevation view thereof. As shown, the distal tip 30 comprises a combination of a mechanical cutting means and a laser ablation means. Mechanical cutting means of FIGS. 5-7 includes a sharp cutting edge or blade 32 that may be parallel to the longitudinal axis of the catheter or it lumen. Laser ablation means of the depicted embodiments comprise an extending spiral or helix-type array of laser emitters provided in an approximate 360 degree pattern about the longitudinal axis of the catheter and its lumen. The helical array comprises a first terminus 38 at a proximal end of the cutting edge 32 and a second terminus 36 at a distal end of the cutting edge 32. Provided interior to the helical array is an inner lumen 40 through which material dislodged or ablated by the mechanical cutting feature and/or the laser emitters 34 is removed from a patient.

In various embodiments, the inner lumen 40 comprises a lumen of substantially circular cross-section with an internal diameter of between approximately 0.050 inches and 0.10 inches. In certain embodiments, the inner lumen comprises a lumen of substantially circular cross-section with an internal diameter of between approximately 0.060 inches and 0.090 inches. In a preferred embodiment, the inner lumen comprises a lumen of substantially circular cross-section with an internal diameter of approximately 0.072 inches. In various embodiments, the distal tip 30 comprises an outer diameter of between approximately 0.080 and 0.10 inches. In preferred embodiments, the distal tip comprises an external diameter of approximately 0.090 inches.

It will be recognized that distal tips 30 of the present disclosure may be provided with any number of laser emitters. However, in a particular embodiment, a distal tip is provided that comprises 50 optical fibers capable of transmitting light of approximately 130 μm wavelength.

The cutting edge or blade of the present disclosure may be constructed of, for example, stainless steels, abrasive materials, diamond tip, etc.

Figure 8:
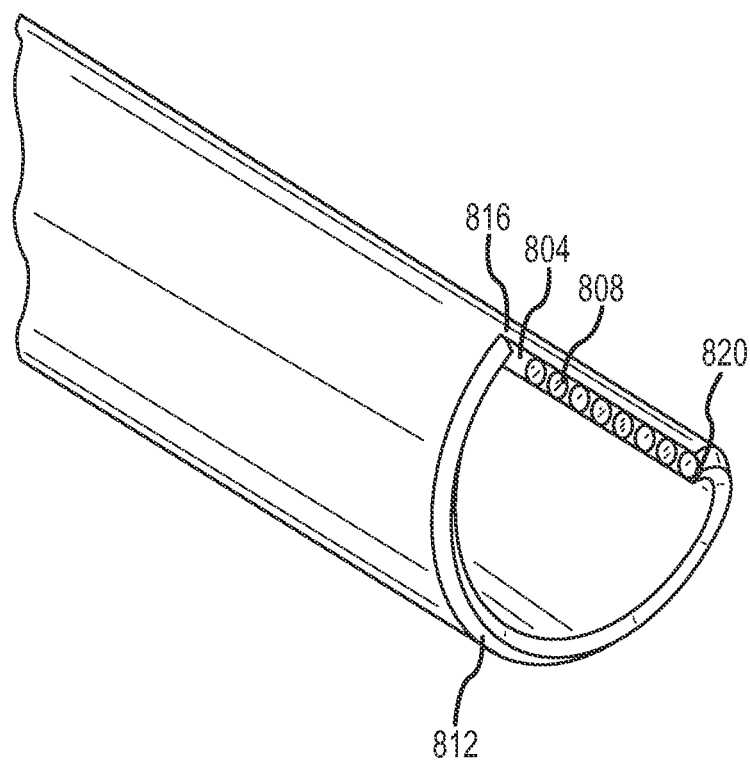
FIG. 8 is a perspective view of a distal end of a catheter according to another embodiment of the present disclosure.

The present disclosure further contemplates that various features of FIGS. 5-7 may be inverted. Referring to FIG. 8, for example, there is depicted in one embodiment, the laser emitters 808 along surface 804 that may be substantially parallel to the longitudinal axis of the catheter. Also included in this embodiment of the distal portion of the catheter is a sharp cutting edge 812 or blade provided in a spiral or helical configuration as it extends from the proximal end 816 of the surface 804 to the distal end 820 of surface 804.

Various distal tip designs are contemplated by the present disclosure. Although particular embodiments are shown and described herein, the present disclosure is not so limited. Features of the present disclosure may be provided in combination with various catheter distal end designs. For example, the configuration of the laser emitters 34 of FIGS. 5-7 may be arranged such that they extend spirally or helically but in a pattern less than 360 degrees. Similarly, the sharp cutting edge or blade 32 in FIGS. 5-7 may be at an angle or offset from the longitudinal axis of the catheter or it lumen.

Catheter distal tips of the present disclosure include, but are not limited to, purely mechanical cutting devices provided in: circular, off-set, and semi-circular arrangements; various combinations of mechanical and laser-ablative cutting systems; and purely laser-ablative cutting systems. For example, FIGS. 5-8 include tips capable of applying laser energy and/or mechanical force (or pressure) to core through lesion material and create plug-type objects that can be aspirated through the catheter in their entirety. However, certain aspects of this disclosure may be beneficial to various mechanical and/or other types of macerating type devices and catheter tips. For example, FIGS. 9 and 10 illustrate mechanical tips that may be used to cut and/or macerate lesion-type tissue that may be capable of being aspirated in the manner discussed within this disclosure.

Figure 9A:
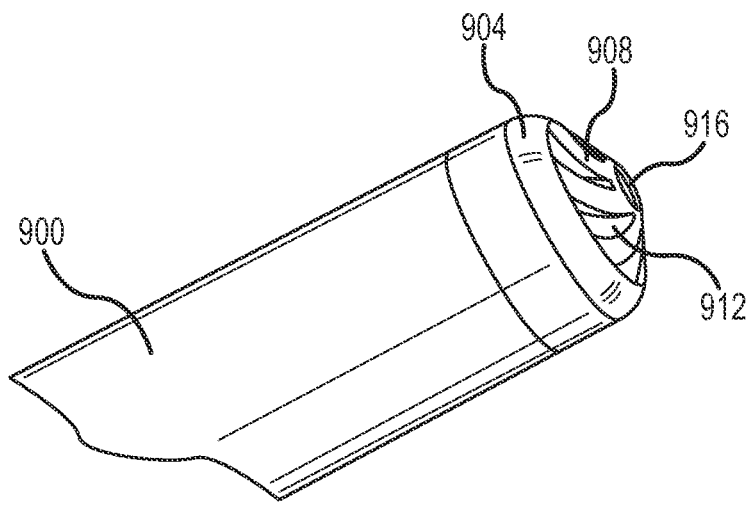
FIG. 9A, is a perspective view of a distal end of a catheter having a cutting blade at its distal tip in a retracted position according to one embodiment of the present disclosure.
Figure 9B:
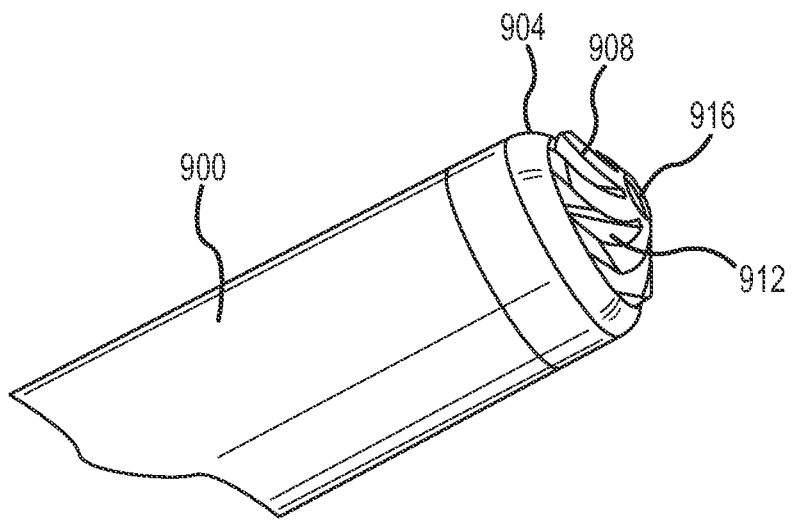
FIG. 9B, is a perspective view of a distal end of a catheter having a cutting blade at its distal tip in an extended position according to one embodiment of the present disclosure.

Referring to FIGS. 9A & 9B, there is depicted a catheter 900 having a tip 904 having a cutting blade with a plurality sharp vanes 908 of capable of cutting and/or macerating lesion tissue. FIG. 9A illustrates the cutting blade in a retracted position so that the catheter can navigate the subject's vasculature with minimal or no exposure of the vanes 908. FIG. 9B illustrates the cutting blade in the extended position. As the cutting blade extends, the vanes 908 extend and rotate, thereby cutting and/or macerating the tissue with which the vanes 908 contact. Additionally, as the vanes 908 are extending and retracting, the pulsed aspiration system (previously discussed) can aspirate the cut and macerated tissue through the openings 912 between the vanes 908, the lumen 916 within the center of the blades and/or both. Furthermore, depending upon the internal configuration of the catheter and the channels to the openings 912 and lumen 916, one or more aspiration systems may be used in conjunction with the catheter.

Figure 10A:
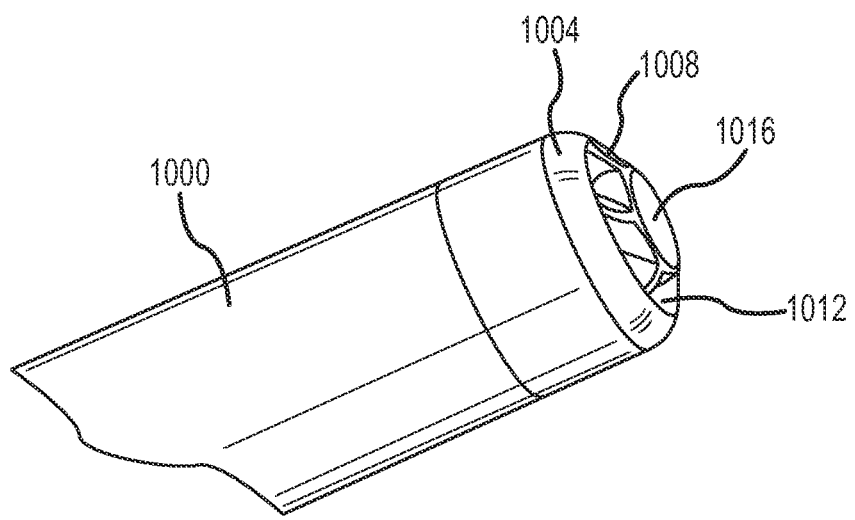
FIG. 10A, is a perspective view of a distal end of a catheter having a cutting blade at its distal tip in a retracted position according to another embodiment of the present disclosure.
Figure 10B:
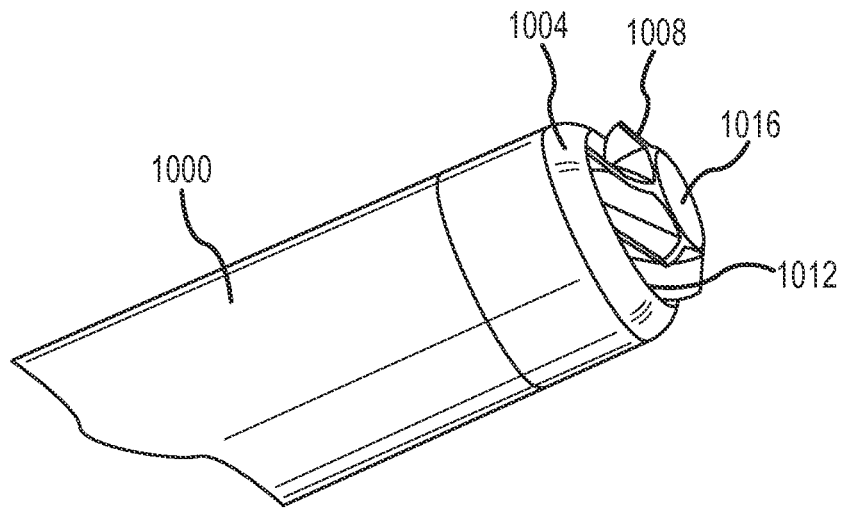
FIG. 10B, is a perspective view of a distal end of a catheter having a cutting blade at its distal tip in an extended position according to another embodiment of the present disclosure.

Depending upon its use, the catheter may have differently shaped cutting blades and vanes. For example, if it is desirable to use a catheter for lead extraction, it may be preferable that the size of the lumen be increased, such as illustrated in FIGS. 10A-10B, thereby altering the size and configuration of the blades. Similar to FIGS. 9A and 9B, FIGS. 10A and 10B depict a catheter 1000 having a tip 1004 having a cutting blade with a plurality sharp vanes 1008 capable of cutting and/or macerating lesion tissue. However, in comparison to FIGS. 9A and 9B, FIGS. 10A and 10B have a larger lumen 1016 and larger openings 1012 between the vanes 1008 because there are fewer vanes. Although these two figures illustrate two types of cutting blades that can be used in conjunction with the aspiration system(s) discussed in this disclosure, those of skill in the art will appreciate that other configurations and types of cutting blades may be used in cooperation therewith. Accordingly, FIGS. 9-10 are not intended to represent the only ways that a mechanical, cutting-type catheter may be configured and constructed, and all such configurations and constructions are within the knowledge of one skilled in the art are considered within the scope of this disclosure.

Figure 11B:
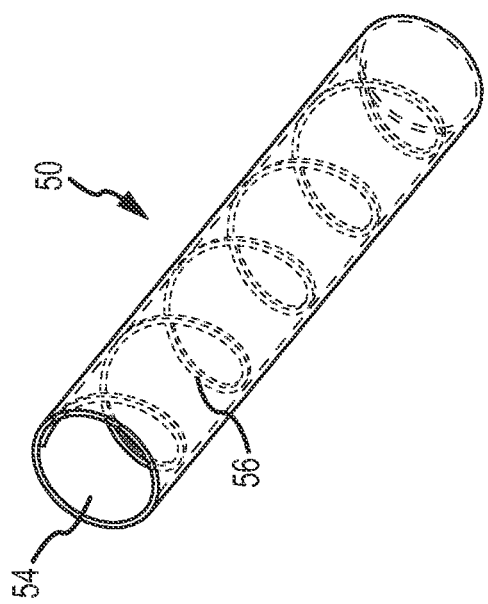
FIG. 11B is a phantom perspective view of a catheter according to one embodiment.
Figure 11A:
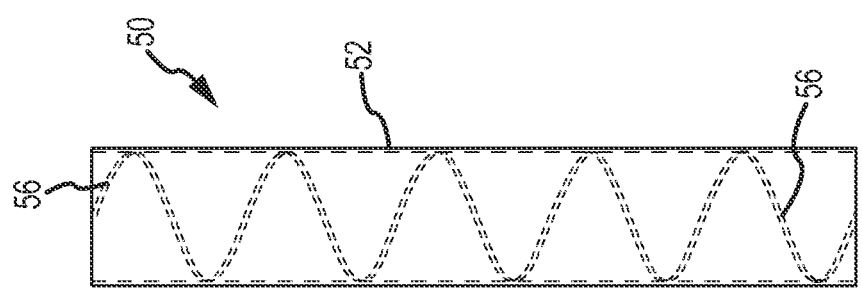
FIG. 11A is a cross-sectional elevation view of a catheter according to one embodiment.

FIG. 11A is a cross-sectional elevation view of one embodiment of a catheter 50 comprising an outer surface 52 and an inner surface 54. The inner surface 54 of the catheter 50 may comprise a helical structure 56 extending from its distal to it proximal ends either continuously or for portions thereof. The helical structure 56 may comprise a polymer extrusion or metal insert extending radially inwardly from an inner diameter of the inner surface 54 and along a length of the catheter 50 in a helical or spiral manner. Alternatively, however, the helical structure 56 is provided as a recessed feature along the internal surface 54 of the catheter 50. As the lesion material, either in the form of a plug or in macerated form enters the lumen formed by the inner surface 54, the helical structure 56 facilitates the spinning of the material within the lumen as it is aspirated, thereby potentially reducing the potential for clogging. Additionally, the helical structure 56 may also macerate or further macerate the material, thereby potentially aiding and/or increasing the material's unimpeded travel from the distal to the proximal end.

A portion of a catheter 50 is depicted in FIGS. 11A-11B and no limitation with respect to which portion or specific length is provided or implied. FIGS. 11A-11B are provided to depict the feature of the helical structure 56 along an internal surface of the catheter 50. Such a structure 56 may be provided along any length of the catheter, including a distal end of the catheter. Additionally, although not depicted in FIGS. 11A-11B, various additional features as shown and described herein may be provided in combination with the features of FIGS. 11A-11B. For example, the catheter 50 may further comprise distal end cutting features such as laser ablative means and/or mechanical as shown and described herein. Additionally, vacuum pulsing and detections systems as shown and described may be provided in combination with the catheter 50. It will be recognized that the helical structure 56 depicted in FIGS. 11A-11B comprises a feature that may be integrated with or provided in combination with various features shown and described herein.

It will be recognized that the helical structure 56 of the catheter 50 generally comprises an internal threaded feature. The helical structure 56 may comprise various different thread characteristics, including overall length, pitch, diameter, etc. Preferably, however, the pitch and ramp angle of the helical structure 56 is shallow enough to effectively ablate occlusions within a blood vessel.

A number of variations and modifications of the disclosure can be used. It would be possible to provide for some features of the disclosure without providing others.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A catheter aspiration system comprising:
   a catheter having a tubular wall and a longitudinal axis, the tubular wall comprising a lumen and a distal end, and an inner band comprising a distal end, the inner band creating an orifice for the lumen at a lumen distal end, the orifice having a first internal diameter, the lumen extending proximally from the inner band and having a second internal diameter, wherein the first internal diameter of the orifice is smaller than the second internal diameter, the lumen having an inner surface comprising a helical structure extending along a length thereof; and a plurality of optical fibers located within the tubular wall, wherein the plurality of optical fibers comprise distal ends, wherein the distal end of the tubular wall, the distal ends of the optical fibers, and the distal end of the inner band terminate at a common plane perpendicular to the longitudinal axis; and
   a vacuum pump in fluid communication with the catheter.

2. The catheter assembly of claim 1, wherein the helical structure projects radially inwardly of the lumen.

3. The catheter assembly of claim 1, wherein the helical structure is embedded within the lumen and extends radially outwardly thereof.

4. The catheter aspiration system of claim 1, further comprising:
   a valve assembly in communication with the vacuum pump, the valve assembly having an open position and closed position; and
   a controller for alternating the position of the valve assembly between the open position and the closed position.

5. The catheter aspiration system of claim 4, wherein the valve assembly comprises a solenoid valve.

6. The catheter aspiration system of claim 5, wherein controller comprises a pulse width modulator.

7. The catheter aspiration system of claim 1, further comprising a filter in fluid communication with the catheter.

8. The catheter aspiration system of claim 1, wherein the inner band comprises a straight interior surface extending from a distal end of the inner band to a proximal end of the inner band.

* * * * *